(12) United States Patent
Ludwig et al.

(10) Patent No.: US 7,998,700 B2
(45) Date of Patent: *Aug. 16, 2011

(54) USE OF A COMPOSITION WHICH REGULATES OXIDATION/REDUCTION REACTIONS INTRACELLULARLY AND/OR EXTRACELLULARY IN A STAINING OR SORTING PROCESS

(75) Inventors: Cindy L. Ludwig, St. Louis, MO (US); Jeffrey A. Graham, Chesterfield, MO (US); Kathleen S. Crowley, Webster Groves, MO (US); Muhammad Anzar, Guelph (CA)

(73) Assignee: Inguran, LLC, Navasota, TX (US)

( * ) Notice: Subject to any disclaimer, the term of this patent is extended or adjusted under 35 U.S.C. 154(b) by 172 days.

This patent is subject to a terminal disclaimer.

(21) Appl. No.: 11/092,509

(22) Filed: Mar. 29, 2005

(65) Prior Publication Data
US 2005/0282245 A1    Dec. 22, 2005

Related U.S. Application Data

(60) Provisional application No. 60/557,441, filed on Mar. 29, 2004.

(51) Int. Cl.
*G01N 1/30* (2006.01)
(52) U.S. Cl. ............... 435/40.5; 435/6; 435/2
(58) Field of Classification Search ............ 435/40.5, 435/2
See application file for complete search history.

(56) References Cited

U.S. PATENT DOCUMENTS

| | | | |
|---|---|---|---|
| 3,005,756 A * | 10/1961 | Van Demark et al. ........... 435/2 |
| 3,791,384 A | 2/1974 | Richter et al. |
| 4,267,268 A | 5/1981 | Nelson, Jr. et al. |
| 4,474,875 A | 10/1984 | Shrimpton |
| 5,135,759 A | 8/1992 | Johnson |
| 5,985,216 A | 11/1999 | Rens et al. |
| 5,990,479 A | 11/1999 | Weiss et al. |
| 5,998,140 A | 12/1999 | Dervan et al. |
| 6,071,689 A | 6/2000 | Seidel et al. |
| 6,090,947 A | 7/2000 | Dervan et al. |
| 6,143,901 A | 11/2000 | Dervan |
| 6,149,867 A | 11/2000 | Seidel et al. |
| 6,207,392 B1 | 3/2001 | Weiss et al. |
| 6,247,323 B1 | 6/2001 | Maeda |
| 6,263,745 B1 | 7/2001 | Buchanan et al. |
| 6,309,815 B1 | 10/2001 | Tash et al. |
| 6,316,234 B1 | 11/2001 | Bova |
| 6,322,901 B1 | 11/2001 | Bawendi et al. |
| 6,326,144 B1 | 12/2001 | Bawendi et al. |
| 6,416,190 B1 | 7/2002 | Grier et al. |
| 6,423,551 B1 | 7/2002 | Weiss et al. |
| 6,432,638 B2 | 8/2002 | Dervan et al. |
| 6,576,291 B2 | 6/2003 | Bawendi et al. |
| 6,849,394 B2 | 2/2005 | Rozeboom et al. |
| 7,015,310 B2 | 3/2006 | Remington |
| 2003/0113765 A1 | 6/2003 | Dempcy et al. |
| 2004/0049801 A1 | 3/2004 | Seidel |
| 2005/0003472 A1 * | 1/2005 | Anzar et al. ............... 435/40.5 |
| 2005/0112541 A1 | 5/2005 | Durack et al. |

FOREIGN PATENT DOCUMENTS

| | | |
|---|---|---|
| WO | WO 99/33956 A1 | 7/1999 |
| WO | WO 01/37655 A1 | 5/2001 |
| WO | WO 01/51612 A | 7/2001 |
| WO | WO 01/68110 A | 9/2001 |
| WO | WO 01/85913 A | 11/2001 |
| WO | WO 02/19594 A | 3/2002 |
| WO | WO 02/41906 A2 | 5/2002 |
| WO | 0243574 A2 | 6/2002 |
| WO | 02077011 A3 | 10/2002 |
| WO | 2004/009237 A2 | 1/2004 |
| WO | WO 2004/087177 A1 | 10/2004 |
| WO | WO 2004/088283 A2 | 10/2004 |

OTHER PUBLICATIONS

Salisbury et al , Journal of Reprodution and Fertility, vol. 6, 1963 p. 351-359.*
De Pauw et al, Biology of Reproduction, 2002, p. 1073-1079.*
Sabuer et al , Journal of Reproduction and Fertility vol. 120, 2000 p. 135-142.*
http://www.specialtymedia.com/05Resources/Protocols/ivfprotocol.htm.*
Schenk, J.L., et al., "Cryopreservation of Flow-Sorted Bovine Spermatozoa," Theriogenology, 1999, 52, pp. 1375-1391.
International Search Report for PCT/US2005/026269 dated Dec. 2, 2005, 7 pages.
D'Occhio, M.J., "Sexing of Sperm in Embryos: Use of Sexed Sperm in AI, IVF, ICSI and Graft," 1999, Animal Breeding Use of New Technologies, Kinghorn, van der Werf and Ryan, Eds., Chapter 1, Introduction and Chapter 19, pp. 247-264.
Garner, D.L., et al., "Viability Assessment of Mammalian Sperm Using SYBR-14 and Propidium Iodide," 1995, Biology of Reproduction, vol. 53, pp. 276-284.
Guthrie, H.D., et al., "Flow Cytometric Sperm Sorting: Effects of Varying Laser Power on Embryo Development in Swine," 2002, Molecular Reproduction and Development, vol. 61, pp. 87-92.
Bencic, D.C., et al., "Carbon Dioxide Reversibly Inhibits Sperm Motility and Fertilizing Ability in Steelhead (*Oncorhynchus mykiss*)," 2000, Fish Physiology and Biochemistry, vol. 23(4), pp. 275-281.
Boatman, D.E., et al., "Bicarbonate Carbon Dioxide Regulation of Sperm Capacitation Hyperactivated Motility and Acrosome Reactions," 1991, Biol of Reprod, vol. 44(5), pp. 806-813.

(Continued)

*Primary Examiner* — Ralph Gitomer
*Assistant Examiner* — Tiffany Gough
(74) *Attorney, Agent, or Firm* — Cindee Ewell; Ryan S. Christensen

(57) ABSTRACT

Staining mixtures comprising viable spermatozoa, a composition which regulates oxidation/reduction reactions intracellularly or extracellularly, and a DNA selective dye are disclosed. The cells contained in such suspensions tend to have a greater capacity for enduring the various process steps typically associated with the sorting of sperm cells into gender enriched populations, thereby resulting in post-sort compositions with an increased number of viable or motile sperm. Processes for staining sperm cells comprising the formation of a staining mixture are also disclosed.

22 Claims, 20 Drawing Sheets

OTHER PUBLICATIONS

Garcia, M.A., et al., "Development of a Buffer System for Dialysis of Bovine Spermatozoa Before Freezing III. Effect of Different Inorganic and Organic Salts on Fresh and Frozen-Thawed Semen," 1989, Theriogenology, vol. 31(5), pp. 1039-1048.

Graves, C.N., et al., "Metabolism of Pyruvate by Epididymal-Like Bovine Spermatozoa," 1964, J Dairy Sci, vol. 47(12), pp. 1407-1411.

Graves, C.N., et al., "Metabolic End-products of Anaerobic Spermatozoan Metabolism," 1966, Nature, vol. 211, pp. 308-309.

Johnson, L.A., "Sex Preselection by Flow Cytometric Separation of X and Y Chromosome-Bearing Sperm Based on DNA Difference: A Review," 1995, Reprod. Fert. Dev., vol. 7, pp. 893-903.

Johnson, L.A., "Sex Preselection: High-Speed Flow Cytometric Sorting of X and Y Sperm for Maximum Efficiency," 1999, Theriogenology, vol. 52(8), pp. 1323-1341.

Karow, A.M. et al., "Effects of Temperature, Potassium Concentration, and Sugar on Human Spermatozoa Motility: A Cell Preservation Model from Reproductive Medicine," 1992, Cryobiology, vol. 29, pp. 250-254.

Lodge, J.R., et al., "Carbon Dioxide in Anaerobic Spermatozoan Metabolism," 1968, vol. 51(1), pp. 96-103.

Salisbury, G.W., Reversal by Metabolic Regulators of CO2-induced Inhibition of Mammalian Spermatozoa, 1959, Proc Soc Exp Biol Med, vol. 101(1), pp. 197-189.

International Search Report for PCT/US2004/009903 dated Aug. 16, 2004, 7 pgs.

International Search Report for PCT/US2004/010481 dated Oct. 10, 2005, 7 pgs.

International Search Report for PCT/US2005/010598 dated Jun. 27, 2005, 7 pgs.

International Search Report for PCT/US2005/010599 dated Dec. 12, 2005, 9 pgs.

Physiology of Reproduction and Artificial Insemination of Cattle, 1978, 2nd Ed., Chap. 16-18, pp. 442-576, Edited by G.W. Salisbury, N.L. VanDemark, J.R. Lodge, published by W.H. Freeman Co., San Francisco, CA.

Baumber, J., et al., "The Effect of Reactive Oxygen Species on Equine Sperm Motility, Viability, Acrosomal Integrity, Mitochondrial Membrane Potential, and Membrane Lipid Peroxidation," J of Andrology, 2000, vol. 21(6), pp. 895-902.

Best, T.P., et al., "Nuclear Localization of Pyrrole-Imidazole Polyamide-Flourescein Conjugates in Cell Culture," PNAS, 2003, vol. 100(21), pp. 12063-12068.

Bruemmer, J.E., et al., "Effect of Pyruvate on the Function of Stallion Spermatozoa Stored for up to 48 Hours," J Anim Sci, 2002, vol. 80, pp. 12-18.

Denniston, D.J., et al., "Effect of Antioxidants on the Motility and Viability of Cooled Stallion Spermatozoa," J Reprod and Fertil, 2001, Supplement 56, pp. 121-126.

Farrell, P.B., et al., "Quantification of Bull Sperm Characteristics Measured by Computer-Assisted Sperm Analysis (CASA) and the Relationship to Fertility," Theriogenology, 1998, vol. 49, pp. 871-879.

Gygi, M.P., et al., "Use of Fluorescent Sequence-Specific Polyamides to Discriminate Human Chromosomes by Microscopy and Flow Cytometry," Nucl Acids Res, 2002, vol. 30(13), pp. 2790-2799.

Johnson, L.A., et al., "Flow Cytometry of X and Y Chromosome-Bearing Sperm for DNA Using an Improved Preparation Method and Staining with Hoechst 33342," Gamete Research, 1987, vol. 17, pp. 203-212.

International Search Report for PCT/US2005/010598, dated Jun. 27, 2005, 5 pages.

Upreti, G. C., et al., Studies on aromatic amino acid oxidase activity in ram spermatozoa: role of pyruvate as an antioxidant, Animal Reproduction Science 51 (1998) 275-287.

Parallel Australian application No. 2005228046, Examiner's Report dated Jan. 25, 2010, 2 pages.

Parallel New Zealand application No. 550197, Notice of Acceptance w/allowed claims Sep. 14, 2009, 7 pages.

Parallel European application No. 05731399.1, Decision to Grant w/allowed claims dated Dec. 17, 2009, 3 pages.

Parallel Chinese application No. 200580017377.7, Office Action dated Oct. 27, 2010, 3 pages (Eng.Transl.).

Parallel Japanese application No. 2007-506488, Office Action dated Dec. 10, 2010, 2 pages.

Baumber, The Effect of Reactive Oxygen Species on Equine Sperm Motility, Viability, Acrosomal Integrity, Mitochondrial Membrane Potential, and Membrane Lipid Peroxidation, Journal of Andrology, vol. 21 No. 6 Nov./Dec. 2000 pp. 895-902.

* cited by examiner

US 7,998,700 B2

USE OF A COMPOSITION WHICH REGULATES OXIDATION/REDUCTION REACTIONS INTRACELLULARLY AND/OR EXTRACELLULARY IN A STAINING OR SORTING PROCESS

REFERENCE TO RELATED APPLICATIONS

This application is a nonprovisional of U.S. patent application Ser. No. 60/557,441, filed Mar. 29, 2004, which is hereby incorporated herein by reference in its entirety.

FIELD OF THE INVENTION

The present invention generally relates to a process of sorting stained sperm cells. More specifically, the present invention relates to processes for sorting sperm cells in which a sperm cell suspension containing a composition which regulates oxidation/reduction reactions intracellularly and/or extracellularly is formed.

BACKGROUND

The fertilization of animals by artificial insemination (AI) and embryo transplant following in vitro fertilization is an established practice. In the livestock production industry, the ability to influence the reproductive outcome toward offspring having one or more desired characteristics has obvious advantages. By way of example, there would be an economic benefit in the dairy industry to preselect offspring in favor of the female sex to ensure the production of dairy cows. The separation of sperm into enriched populations of X and Y chromosome-bearing cells, known as gender enriched semen or gender enriched sperm, is one method of achieving preselected offspring.

In order to obtain gender enriched semen, sperm cells must be stained with a dye and subsequently sorted into X and Y chromosome-bearing cells. Each of staining and sorting processes places a stress on the sperm cells that decreases sperm cell viability or motility, particularly progressive motility. Especially stressful is the process of staining the sperm cells, which requires contacting the cells at with a dye for a certain period of time, often at a temperature and pH which are not common in the typical sperm cell environment.

SUMMARY OF THE INVENTION

Among the various aspects of the present invention are sperm suspensions having utility, for example, in processes used to sort sperm into enriched populations of X or Y-chromosome bearing sperm.

Briefly, therefore, the present invention is directed to a staining mixture comprising viable spermatozoa, a composition which regulates oxidation/reduction reactions intracellularly and/or extracellularly, and a DNA selective dye, the concentration of the composition in the staining mixture being greater than 50 μM when the composition is pyruvate.

The present invention is further directed to a process for staining sperm cells, the process comprising forming a staining mixture containing intact viable sperm cells, a composition which regulates oxidation/reduction reactions intracellularly and/or extracellularly, and a DNA selective dye, the concentration of the composition in the staining mixture being greater than 50 μM when the composition is pyruvate.

DETAILED DESCRIPTION OF THE INVENTION

Figure 1:
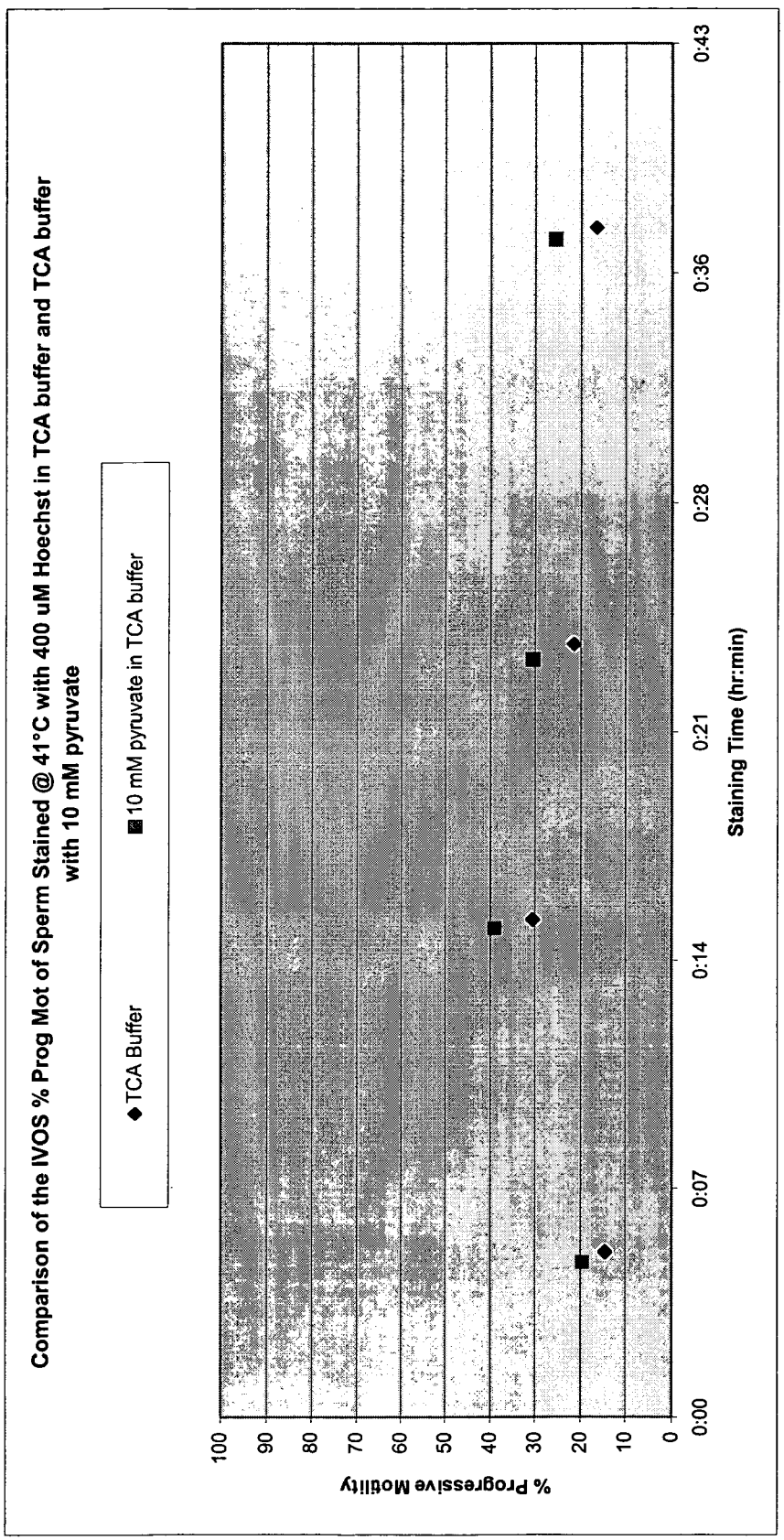
FIG. 1 graphically depicts the results of the study carried out in Example 1 wherein percent progressive motility of sperm is measured for sperm stained with 400 μM Hoechst 33342 dye at 41° C. in either a TCA buffer or a TCA buffer containing 10 mM pyruvate.

Surprisingly, it has been determined that spermatozoa contacted with a composition which regulates oxidation/reduction reactions intracellularly and/or extracellularly tend to have a greater capacity for enduring the various process steps typically associated with the sorting of sperm cells into an enriched population of X or Y chromosome-bearing spermatozoa. In a preferred embodiment, therefore, gender enriched populations of spermatozoa may be prepared for artificial insemination which have an increased number of viable cells or an increased number of motile sperm, particularly progressively motile sperm, in a post-stain or post-sort composition.

In general, a composition which regulates oxidation/reduction reactions intracellularly and/or extracellularly is a composition comprising a component that can transfer electrons from one substance to another. Such a composition may comprise a component that either gains or scavenges electrons (an oxidizing agent or electron acceptor) or a component that donates electrons (a reducing agent or electron donor). With respect to biological systems, a composition which regulates oxidation/reduction reactions intracellularly and/or extracellularly is more easily understood to be a composition that either adds or removes an oxygen or hydrogen from a compound.

Generally, therefore, such a composition may comprise, for example, pyruvate, vitamin K, lipoic acid, glutathione, flavins, quinones, superoxide dismutase (SOD), and SOD mimics. Such a composition may be present in sperm suspension in a concentration sufficient to effect the protective effect without detrimentally affecting sperm health. Exemplary concentration ranges include from about 10 μM to about 50 mM depending upon such factors as the particular composition being used or the concentration of sperm in the suspension. For example, if pyruvate is included in the composition, it may be present in the sperm suspension in a concentration from about 0.5 μM to about 50 mM, preferably from about 1 mM to about 40 mM, more preferably from about 2.5 mM to about 25 mM, still more preferably from about 10 mM to about 20 mM, even still more preferably at about 15 mM, and most preferably at about 10 mM. If vitamin K is included in the composition, it may be present in the sperm suspension in a concentration from about 1 μM to about 100 μM, preferably from about 10 μM to about 100 μM, more preferably from about 50 μM to about 100 μM, and most preferably at about 100 μM. If lipoic acid is included in the composition, it may be present in the sperm suspension in a concentration from about 0.1 mM to about 1 mM, preferably from about 0.5 mM to about 1 mM, more preferably about 0.5 mM, and most preferably about 1 mM. The sperm suspension may comprise any one of the above listed embodiments of the composition or any combination thereof in the above listed concentrations. For example, the sperm suspension may comprise a composition which regulates oxidation/reduction reactions intracellularly and/or extracellularly comprising pyruvate in a concentration of about 10 mM and vitamin k in a concentration of about 100 μM. Alternatively, the sperm suspension may comprise a composition comprising pyruvate in a concentration of about 10 mM and lipoic acid in a concentration of about 1 mM. Yet another example includes a sperm suspension comprising a composition comprising pyruvate in a concentration of about 10 mM, vitamin K in a concentration of about 100 μM, and lipoic acid in a concentration of about 1 mM.

Generally, a composition which regulates oxidation/reduction reactions intracellularly and/or extracellularly may provide a protective effect such as an increase in the number of viable cells or an increase in the number of motile cells, particularly progressively motile cells, in the sperm suspension containing the composition. While such a composition provides a protective effect to any suspension formed in the process of sorting sperm cells, the benefit is of particular value during the staining step, wherein such a composition may help to maintain sperm viability at elevated staining temperatures, at elevated dye concentrations, at increased staining periods, or any combination thereof.

In general, the cell sorting process comprises a series of discrete steps, i.e., collection of a cell sample, staining of the cells, sorting of the cells, collection of the sorted cells, and optionally, cryoextension of the sorted cells. Advantageously, the composition which regulates oxidation/reduction reactions intracellularly and/or extracellularly may be included in sperm suspensions formed or employed in one or more of these steps.

Collection of the Cell Sample

Intact viable bovine, porcine, equine, or other mammalian sperm cells, may be collected and contacted with the motility inhibitor. Various methods of collection of viable sperm are known and include, for example, the gloved-hand method, use of an artificial vagina, and electro-ejaculation. As an example, a bovine semen sample, typically containing about 0.5 to about 10 billion sperm cells per milliliter, may be collected directly from the source mammal into a vessel containing a composition which regulates oxidation/reduction reactions intracellularly and/or extracellularly to form a sperm suspension. Alternatively, the semen sample may be collected into an empty vessel and then subsequently contacted with such a composition within several hours after collection to form the sperm suspension.

The sperm sample may also be combined with a buffer (in the form of a solid or solution) to form a buffered sperm suspension. Among other things, the buffer may enhance sperm viability by buffering the suspension against significant changes in pH or osmotic pressure. Generally, a buffer is non-toxic to the cells and is compatible with the dye used to stain the cells. Exemplary buffers include phosphates, diphosphates, citrates, acetates, lactates, and combinations thereof. Presently preferred buffers include TCA, TEST, sodium citrate, HEPES, TL, TES, citric acid monohydrate, HEPEST (Gradipore, St. Louis, Mo.), PBS (Johnson et al., *Gamete Research,* 17:203-212 (1987)), and Dulbecco's PBS (Invitrogen Corp., Carlsbad, Calif.).

One or more buffers may be combined together or with additives as discussed below to form a buffered solution, and the buffered solution combined with the sperm sample to form a buffered sperm suspension. A buffered solution may also contain one or more additives, as described in greater detail below, or a composition which regulates oxidation/reduction reactions intracellularly and/or extracellularly. Exemplary buffered solutions are described in Table I. Preferred buffered solutions include a solution comprising 3% TRIS base, 2% citric acid monohydrate, and 1% fructose (w/v) in water at a pH of about 7.0, a solution designated as TCA #1 in Table I, and a solution designated as TCA #2 in Table I.

The amount of buffer employed generally depends upon several considerations, e.g., the particular buffer and the desired sperm concentration (# sperm/ml) in the buffered sperm suspension. Therefore, a sufficient amount of buffer will be used such that the desired concentration of sperm/ml is achieved. Buffer may be added to achieve a sperm suspension that contains from about $1\times10^3$ sperm/ml to about $5\times10^{10}$ sperm/ml. For example, in one embodiment buffer may be added to achieve a "relatively low" concentration of sperm in the sperm suspension, i.e., buffer is added to achieve a sperm suspension that contains less than about $1\times10^7$ sperm/ml, preferably less than about $1\times10^6$ sperm/ml, more preferably about $1\times10^3$ to about $5\times10^6$ sperm/ml, still more preferably about $1\times10^3$ to about $1\times10^6$ sperm/ml, even more preferably about $1\times10^4$ to about $1\times10^5$ sperm/ml, and most preferably about $1\times10^5$ sperm/ml. In an alternative embodiment, buffer may be added to achieve an "intermediate" concentration of sperm in the sperm suspension, i.e., buffer is added to achieve a sperm suspension that contains about $1\times10^7$ to about $1\times10^8$ sperm/ml. In yet another alternative embodiment, buffer may be added to achieve a "relatively high" concentration of sperm in the sperm suspension, i.e., buffer is added to achieve a sperm suspension that contains greater than about $1\times10^5$ sperm/ml, preferably about $1\times10^8$ to about $5\times10^{10}$ sperm/ml, more preferably about $1.5\times10^8$ to about $2\times10^{10}$ sperm/ml, even more preferably about $1.5\times10^8$ to about $2\times10^8$ sperm/ml, and still more preferably about $1.5\times10^8$ sperm/ml.

An additional consideration in determining the amount of buffer employed, i.e., whether the buffered sperm suspension will have a "relatively low," an "intermediate," or a "relatively high" concentration of sperm in the sperm suspension,

TABLE I

Buffered Solutions

| COMPONENTS | TCA#1 | TCA#2 | TEST | Na Citrate | HEPES | TL |
|---|---|---|---|---|---|---|
| Sodium chloride (NaCl) | | | | | 7.6 g | 5.84 g |
| Potassium chloride (KCl) | | | | | 0.3 g | 0.23 g |
| Sodium bicarbonate (NaHCO3) | | | | | | 2.1 g |
| Sodium phosphate monobasic (NaH2PO4-H2O) | | | | | | 0.04 g |
| (+)-2-hydroxyproprionic acid (Na Lactate) | | | | | | 3.68 ml |
| Magnesium chloride (MgCl2) | | | | | 0.1 g | 0.08 g |
| N-(2-hydroxyethyl)piperazine-N'-(2-ethansulfonic acid) (HEPES) | | | | | 2.38 g | 2.38 g |
| tris(hydroxymethyl) amimonethane (TRIS base) | 30.3 g | 32.02 g | 10.28 g | | | |
| Citric Acid Monohydrate | 15.75 g | 18.68 g | | | | |
| Na Citrate Dihydrate | | | | 29 g | | |
| 2-[(2-hydroxy-1,1-bis[hydroxymethyl]ethyl) aminoethanesulfonic acid (TES) | | | 43.25 g | | | |
| Fructose | 12.5 g | 2.67 g | | 10 g | 2.52 g | |
| D-Glucose | | | 2 g | | | |
| Steptamycin | | | 0.25 g | | | |
| Penicillin-G | | | 0.15 g | | | |
| Water | 1 liter | 1 liter | 1 liter | 1 liter | 1 liter | 1 liter |
| Target pH | 7.35 | 7.35 | 7.35 | 7.35 | 7.35 | 7.35 |
| Target osmolality (milliosmols/kg H2O) | ~314 | ~300 | ~302 | ~316 | ~298 | ~296 | includes the method by which the sperm cells may be subsequently sorted or enriched. For example, the sperm cells may be sorted using flow cytometry as described in greater detail below. In such an instance, the buffered sperm suspension may typically be of an "intermediate" or "relatively high" concentration of sperm/ml. Other sorting or enrichment techniques may benefit from a lesser concentration of sperm cells, such as a "relatively low" concentration of sperm cells, labeled with a marker, such as for example the dyes and labels described herein.

Alternatively, the sperm may be combined with an inhibitory buffer to form an inhibited sperm suspension. Inhibitory buffers cause the sperm cells to emulate sperm cells of the epididymis of a mammal, such as for example a bull, by simulating the fluid environment of the epididymis or epididymal tract of the mammal. Such a buffer would reduce or inhibit the motility or metabolic activity of the sperm. Exemplary buffers of this class include carbonate based buffers, such as for example those disclosed in Salisbury & Graves, J. Reprod. Fertil., 6:351-359 (1963). A preferred buffer of this type comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water). In addition, the inhibited sperm suspension may also contain a composition which regulates oxidation/reduction reactions intracellularly and/or extracellularly.

In addition to a buffer, the sperm suspension may also contain a range of additives to enhance sperm viability or motility or to provide other benefits. Exemplary additives include energy sources, protein sources, and antibiotics. One or more of these additives may be introduced into the buffer or buffered solution before the formation of the buffered sperm suspension or, alternatively, may be separately introduced into the sperm suspension.

One or more energy sources may be added to minimize or inhibit the sperm cells from oxidizing intracellular phospholipids and other cellular components. Exemplary energy sources include monosaccharides, such as fructose, glucose, galactose and mannose, and disaccharides, such as sucrose, lactose, maltose, and trehalose, as well as other polysaccharides. For example, the resulting sperm suspension may include about 1% (w/v) to about 4% (w/v) of the energy source(s). If included, the energy source is preferably fructose and the sperm suspension contains about 2.5% (w/v).

To minimize dilution shock, provide support to the cells, or disperse the cells throughout the suspension, a protein source may also be included in the buffer, buffered solution, sperm suspension, or buffered sperm suspension. Exemplary protein sources include egg yolk, egg yolk extract, milk (including heat homogenized and skim), milk extract, soy protein, soy protein extract, serum albumin, bovine serum albumin, human serum substitute supplement, and combinations thereof. Albumin, and more particularly bovine serum albumin (BSA), is a preferred protein source. For example, if included, BSA may be present in the sperm suspension in an amount of less than about 5.0% (w/v), preferably less than about 2% (w/v), more preferably less than about 1% (w/v), and most preferably in an amount of about 0.1% (w/v).

The use of a protein source, such BSA, alone may initiate the process of capacitation in a percentage of the sperm cells in the suspension. It is preferred that this process take place in the female reproductive tract. Therefore, in order to inhibit the initiation of capacitation during dilution, as well as during the subsequent staining and sorting, an alternative protein source or a protein substitute may be included in the sperm suspension. The alternative protein source or protein substitute possess the advantageous effects of a typical protein source, such as BSA, in addition to the ability to inhibit the initiation of capacitation in a larger percentage of the cells in the sperm suspension. Examples of an alternative protein source include human serum substitute supplement (SSS) (Irvine Scientific, Santa Ana, Calif.) and cholesterol enhanced BSA, while an example of a protein substitute includes a polyvinyl alcohol, such as for example, a low to medium viscosity polyvinyl alcohol generally of a molecular weight of about 30,000 to about 60,000. Generally, if included, these compositions will be present in the same amounts as disclosed above with respect to BSA, with the total albumin content of the buffer or buffered solution generally not exceeding about 5.0% (w/v).

An antibiotic may be added to the sperm suspension or buffered sperm suspension in order to inhibit bacterial growth. Exemplary antibiotics include, for example, tylosin, gentamicin, lincomycin, spectinomycin, Linco-Spectin® (lincomycin hydrochloride-spectinomycin), penicillin, streptomycin, ticarcillin, or any combination thereof. The antibiotics may be present in a concentration of about 50 μg to about 800 μg per ml of semen, regardless of whether the semen is neat, buffered, or contains additional substances, such as for example, any of the additives mentioned herein. The Certified Semen Services (CSS) and National Association of Animal Breeders (NAAB) have promulgated guidelines regarding the use of antibiotics with respect to sperm collection and use.

Staining of the Cells

A composition which regulates oxidation/reduction reactions intracellularly and/or extracellularly may be used in the process of staining the cells. Generally, a process of staining sperm cells may comprise the formation of a staining mixture, sometimes referred to as a labeling mixture, containing intact viable sperm cells, a composition which regulates oxidation/reduction reactions intracellularly and/or extracellularly, and a dye, sometimes referred to as a label. In this aspect of the invention, the composition may be contacted with the sperm cells to form a sperm suspension, and then the suspension contacted with a DNA selective dye. In this embodiment, the sperm source may be neat semen, or alternatively, a sperm-containing semen derivative obtained by centrifugation or the use of other means to separate semen into fractions.

Once obtained, the sperm cells may be introduced into the staining mixture in the form of neat semen or in the form of a suspension derived therefrom, e.g., a sperm suspension or a buffered sperm suspension as discussed above with respect to collection of the cell sample.

The dye may be in the form of a neat solid or a liquid composition. The dye may also be dissolved or dispersed in an unbuffered liquid to form a dye solution. Alternatively, the dye may be in the form of a dye suspension comprising a dye and a buffer or buffered solution that is biologically compatible with sperm cells. A range of exemplary buffers and buffered solutions are discussed above with respect to sample collection. For example, among the buffers which may be used is a TCA buffer solution comprising 3% TRIS base, 2% citric acid monohydrate, and 1% fructose in water at a pH of about 7.0, or a carbonate-based buffer solution comprising 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water). Thus, for example, a staining mixture may be formed by combining neat semen with a dye and a composition which regulates oxidation/reduction reactions intracellularly and/or extracellularly. Alternatively, the staining mixture may be formed by combining neat semen with a buffer or buffered solution, a dye, and a composition which regulates oxidation/reduction reactions intracellularly and/or extracellularly.

Additionally, the staining mixture may be formed by combining a sperm suspension with a dye.

The staining mixture may be formed by using one or more UV or visible light excitable, DNA selective dyes as previously described in U.S. Pat. No. 5,135,759 and WO 02/41906. Exemplary UV light excitable, selective dyes include Hoechst 33342 and Hoechst 33258, each of which is commercially available from Sigma-Aldrich (St. Louis, Mo.). Exemplary visible light excitable dyes include SYBR-14, commercially available from Molecular Probes, Inc. (Eugene, Oreg.) and bisbenzimide-BODIPY® conjugate 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl(3-[({4-[6-(4-methylpiperazin-1-yl)-1H,3'H-2,5'-bibenzimidazol-2'-yl]phenoxylacetyl)amino]propyl}amino)propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm cells to an unacceptable degree when used in concentrations which enable sorting as described elsewhere.

Alternatively, the staining mixture may be formed using fluorescent polyamides, and more specifically polyamides with a fluorescent label or reporter conjugated thereto. Such labels will fluoresce when bound to nucleic acids. Examples of polyamides with a fluorescent label or reporter attached thereto include, for example, those disclosed in Best et al., *Proc. Natl. Acad. Sci. USA*, 100(21): 12063-12068 (2003); Gygi, et al., *Nucleic Acids Res.*, 30(13): 2790-2799 (2002); U.S. Pat. No. 5,998,140; U.S. Pat. No. 6,143,901; and U.S. Pat. No. 6,090,947, the content of each of which is hereby incorporated herein by reference.

Fluorescent nucleotide sequences may also be used to label the sperm cells. Such nucleotide sequences fluoresce when hybridized to a nucleic acid containing a target or complementary sequence, but are otherwise non-fluorescent when in a non-hybridized state. Such oligonucleotides are disclosed, for example, in U.S. patent application Publication No. 2003/0113765 (hereby incorporated herein by reference).

Sex specific antibodies may also be used to label the sperm cells in a staining mixture. In this embodiment, for example, a sex specific antibody may be conjugated with a fluorescent moiety (or equivalent reporter molecule). Because the antibody binds to antigens present on only an X chromosome-bearing or, alternatively, a Y chromosome-bearing cell, such cells can be selectively identified based upon their fluorescence (versus the non-fluorescence of an unlabeled cell). Moreover, more than one sex specific antibody, each antibody having a different fluorescent moiety attached thereto, may be used simultaneously. This allows for differentiation of X chromosome-bearing and Y chromosome-bearing cells based upon the differing fluorescence of each.

Luminescent, color-selective nanocrystals may also be used to label sperm cells in a staining mixture. Also referred to as quantum dots, these particles are well known in the art, as demonstrated by U.S. Pat. No. 6,322,901 and U.S. Pat. No. 6,576,291, each of which is hereby incorporated herein by reference. These nanocrystals have been conjugated to a number of biological materials, including for example, peptides, antibodies, nucleic acids, streptavidin, and polysaccharides, (see, for example, U.S. Pat. Nos. 6,207,392; 6,423,551; 5,990,479, and 6,326,144, each of which is hereby incorporated herein by reference), and have been used to detect biological targets (see, for example, U.S. Pat. Nos. 6,207,392 and 6,247,323, each of which is hereby incorporated herein by reference).

The preferred concentration of the DNA selective dye in the staining mixture is a function of a range of variables which include the permeability of the cells to the selected dye, the temperature of the staining mixture, the amount of time allowed for staining to occur, and the degree of enrichment desired in the subsequent sorting step. In general, the dye concentration is preferably sufficient to achieve the desired degree of staining in a reasonably short period of time without substantially detrimentally affecting sperm viability. For example, the concentration of Hoechst 33342, Hoechst 33258, SYBR-14, or BBC in the staining mixture will generally be between about 0.1 µM and about 1.0M, preferably from about 0.1 µM to about 700 µM, and more preferably from about 100 µM to about 200 µM. In a particularly preferred embodiment, the concentration of Hoechst 33342, Hoechst 33258, SYBR-14, or BBC in the staining mixture will generally be between about 400 µM to about 500 µM, and most preferably about 450 µM. Accordingly, under one set of staining conditions, the concentration of Hoechst 33342 is preferably about 100 µM. Under another set of staining conditions, the concentration of Hoechst 33342 is about 150 µM. Under still another set of staining conditions the concentration is preferably about 200 µM. Under yet another set of staining conditions the concentration of Hoechst 33342 is most preferably about 450 µM.

As another example, the concentration of a fluorescent polyamide, such as for example, those described in U.S. application Publication No. 2001/0002314, will generally be between about 0.1 µM and about 1 mM, preferably from about 1 µM to about 1 mM, more preferably about 5 µM to about 100 µM, even more preferably about 10 µM.

In addition to buffer, other additives may be included in the staining mixture to enhance the viability or motility of the sperm; these additives may be provided as part of the sperm source, the dye source, or separately to the staining mixture. Such additives include energy sources, antibiotics, and seminal plasma, the first two of which are discussed above with respect to collection of the cell sample, and the last of which is discussed below with respect to collection of the sorted cells. Such additives may be added during the staining techniques in accordance therewith.

The staining mixture may be maintained at any of a range of temperatures; typically, this will be within a range of about 4° C. to about 50° C. For example, the staining mixture may be maintained at a "relatively low" temperature, i.e., a temperature of about 4° C. to about 30° C.; in this embodiment, the temperature is preferably from about 20° C. to about 30° C., more preferably from about 25° C. to about 30° C., and most preferable at about 28° C. Alternatively, the staining mixture may be maintained within an "intermediate" temperature range, i.e., a temperature of about 30° C. to about 39° C.; in this embodiment, the temperature is preferably at about 34° C. to about 39° C., and more preferably about 37° C. In addition, the staining mixture may be maintained within a "relatively high" temperature range, i.e., a temperature of about 40° C. to about 50° C.; in this embodiment, the temperature is preferably from about 40° C. to about 45° C., more preferably from about 40° C. to about 43° C., and most preferably at about 41° C. Selection of a preferred temperature generally depends upon a range of variables, including for example, the permeability of the cells to the dye(s) being used, the concentration of the dye(s) in the staining mixture, the amount of time the cells will be maintained in the staining mixture, and the degree of enrichment desired in the sorting step.

Uptake of dye by the sperm cells in the staining mixture is allowed to continue for a period of time sufficient to obtain the desired degree of DNA staining. That period is typically a period sufficient for the dye to bind to the DNA of the sperm cells such that X and Y chromosome-bearing sperm cells may be sorted based upon the differing and measurable fluorescence intensity between the two. Generally, this will be no more than about 160 minutes, preferably no more than about 90 minutes, still more preferably no more than about 60 minutes, and most preferably from about 5 minutes to about 40 minutes.

Accordingly, in one embodiment, a staining mixture is formed comprising sperm cells, a dye in a concentration from about 100 µM to about 200 µM, and a composition which regulates oxidation/reduction reactions intracellularly and/or extracellularly, and the staining mixture is held for a period of time at a temperature of about 41° C. In another embodiment, the composition which regulates oxidation/reduction reactions intracellularly and/or extracellularly comprises pyruvate in a concentration of about 10 mM, vitamin K in a concentration of about 100 µM, or lipoic acid in a concentration of about 1 mM.

In still another embodiment, a staining mixture is formed comprising sperm cells, a dye in a concentration from about 100 µM to about 200 µM, and a composition which regulates oxidation/reduction reactions intracellularly and/or extracellularly, and the staining mixture is held for a period of time at a temperature of about 28° C. In another embodiment, the a composition which regulates oxidation/reduction reactions intracellularly and/or extracellularly comprises pyruvate in a concentration of about 10 mM, vitamin K in a concentration of about 100 µM, or lipoic acid in a concentration of about 1 mM.

In yet another example, a staining mixture is formed comprising sperm cells, a buffer comprising 0.204 g $NaHCO_3$, 0.433 g $KHCO_3$, and 0.473 g $C_6H_8O_7 \cdot H_2O$ per 25 mL of purified water (0.097 moles/L of $NaHCO_3$, 0.173 moles/L of $KHCO_3$, 0.090 moles/L $C_6H_8O_7 \cdot H_2O$ in water), a dye in a concentration from about 100 µM to about 200 µM, and a composition which regulates oxidation/reduction reactions intracellularly and/or extracellularly, and the staining mixture is held for a period of time at a temperature of about 28° C. In another embodiment, the staining mixture is held for a period of time at a temperature of about 41° C. In yet another embodiment, the composition which regulates oxidation/reduction reactions intracellularly and/or extracellularly comprises pyruvate in a concentration of about 10 mM, vitamin K in a concentration of about 100 µM, or lipoic acid in a concentration of about 1 mM.

Sorting

A composition which regulates oxidation/reduction reactions intracellularly and/or extracellularly may also be used during sorting of the sperm cells. Generally, once the sperm are stained according to the present invention, they may be sorted according to any known means that allows for separation based upon fluorescence. Commonly used and well known methods include flow cytometry systems, as exemplified by and described in U.S. Pat. Nos. 5,135,759, 5,985,216, 6,071,689, 6,149,867, and 6,263,745, International Patent Publications WO 99/33956 and WO 01/37655, U.S. patent application Ser. No. 10/812,351 and corresponding International Patent Publication WO 2004/088283.

According to the above-referenced flow cytometry methods, the stained cells are introduced as a sample fluid into the nozzle of a flow cytometer as described in Exhibit A. In one embodiment, therefore, the sample fluid may comprise the stained sperm cells and a composition which regulates oxidation/reduction reactions intracellularly and/or extracellularly.

The sample fluid is typically surrounded by a sheath fluid. The sheath fluid permits the sperm cells in the sample fluid to be drawn out into a single file line. The sheath fluid is collected along with the sperm cells by the collection system of the flow cytometer and therefore forms part of the post-sort environment for the sperm cells. Thus, it is desirable that the sheath fluid provides a protective effect to the cells upon contact of cells by the sheath fluid.

Accordingly, the sheath fluid generally comprises a buffer or buffered solution and a composition which regulates oxidation/reduction reactions intracellularly and/or extracellularly. Examples of buffers and buffered solutions and illustrative concentrations of the same that may be used in the sheath fluid are disclosed above with respect to sample collection and dilution. In a particular embodiment, the sheath fluid comprises 0.96% Dulbecco's phosphate buffered saline (w/v), 0.1% BSA (w/v), in water at a pH of about 7.0.

Optionally, the sheath fluid may also contain a range of additives that are beneficial to sperm viability or motility. Such additives include, for example, an energy source, a protein source, an antibiotic, and polyvinyl alcohol. Each of these additives, and examples of the same, is discussed above with respect to collection of the cell sample. Such additives may be added to the sheath fluid in accordance therewith.

The sheath fluid may optionally be filtered prior to the sorting step. Contaminants that may be present in the sheath fluid, such as non-soluble particulates, may interfere with sorting. Therefore, the sheath fluid may be filtered prior to its introduction into a flow cytometer. Such filters and methods of using the same are well known in the art. Generally, the filter is a membrane of about 0.1 microns to about 0.5 microns, preferably about 0.2 microns to about 0.3 microns, and more preferably about 0.2 microns.

The stained cells may be introduced into the sheath fluid at any time subsequent to staining. Typically, a stream of the stained cells in the sample fluid is injected into a stream of sheath fluid within the nozzle of the flow cytometer. Initially, there is substantially no contacting of the sample fluid and the sheath fluid due to laminar flow of the fluids as discussed in more detail below. It is desirable that the sample fluid and the sheath fluid remain as substantially discrete flowing streams until after the particles (e.g., the stained sperm cells) in the sample fluid have been analyzed. At some point, however, the sheath fluid and the cells of the sample fluid come in contact with one another. For instance in a droplet sorting flow cytometer (discussed below) the sheath fluid and sample fluid begin contacting one another as droplets are being formed downstream of the interrogation location.

At the time of the introduction of the stained cells and the sheath fluid, both the stained cells and the sheath fluid may be at a temperature from about 4° C. to about 50° C. The sheath fluid and the stained cells may be at the same or at different temperatures, with either being at a higher temperature than the other. Accordingly, in one embodiment, at the time of the introduction of the stained cells and the sheath fluid, both the cells and the sheath fluid are at the same temperature; for example, at a "relatively low" temperature, such as for example at about 5° C. to about 8° C.; at an "intermediate" temperature, such as for example at about 25° C. to about 30° C.; or at a "relatively high" temperature, such as for example at about 40° C. to about 43° C. In another embodiment, the stained cells are at a higher temperature than the sheath fluid, such as for example, the cells being at about 40° C. to about 43° C. and the sheath fluid being at about room temperature or at about 5° C. In yet another embodiment, the stained cells are at a lower temperature than the sheath fluid.

Collection of the Sorted Cells

Once sorted, the sorted cells are collected in a vessel that contains a collection fluid. Generally, the purpose of the collection fluid includes cushioning the impact of the sperm cells with the collection vessel or providing a fluid support for the cells. Accordingly, the collection fluid may comprise a composition which regulates oxidation/reduction reactions intracellularly and/or extracellularly, a buffer or buffered solution, and a protein source.

If included, examples of buffers or buffered solutions that may be used in the collection fluid are disclosed above with respect to collection of the sample cells. Typically, these buffers or buffer solutions will be in a concentration of about 0.001M to about 1.0M and have a pH of about 4.5 to about 8.5, preferably of about 5.0 to about 8.0, more preferably of about 5.5 to about 7.5, still more preferably of about 6.0 to about 7.0, even more preferably of about 6.5 to about 7.0, and most preferably of about 6.5. In one embodiment, the collection fluid contains buffer comprising 0.96% Dulbecco's PBS (w/v) at a pH of about 7.0. In another embodiment, the collection fluid contains buffer comprising 0.96% Dulbecco's PBS (w/v) at a pH of about 6.5. In another embodiment, the collection fluid contains a buffer solution comprising 0.204 g $NaHCO_3$, 0.433 g $KHCO3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

If included, the protein source may be any protein source that does not interfere with the viability of the sperm cells and is compatible with the particular buffer or buffered solution being used. Examples of common protein sources include milk (including heat homogenized and skim), milk extract, egg yolk, egg yolk extract, soy protein and soy protein extract. Such proteins may be used in a concentration from about 1% (v/v) to about 30% (v/v), preferably from about 10% (v/v) to about 20% (v/v), and more preferably about 10% (v/v). While milk may be used in combination with a buffer or buffered solution, generally milk is used in the absence of the same, as milk is a solution itself that may serve the same purpose of a buffer or buffered solution. In such instances, the collection fluid may contain about 80% (v/v) to about 90% (v/v) milk.

In addition to or in lieu of the protein source, the collection fluid may also comprise seminal plasma. Seminal plasma serves the dual benefits of improving sperm viability and motility and of stabilizing the sperm membrane (thereby preventing capacitation during the collection and storage of the sperm). Maxwell et al., *Reprod. Fert. Dev.* (1998) 10: 433-440. The seminal plasma may be from the same mammal from which the semen sample was obtained, from a different mammal of the same species, or from a mammal of a different species. If included in the collection fluid, typically the percentage of seminal plasma will be in the range of about 0.5% (v/v) to about 10% (v/v). If used in combination with a protein source, such as for example egg yolk or milk, the total percentage of seminal plasma and protein source will range from about 1% (v/v) to about 30% (v/v). In such instances, the percentage of seminal plasma will be inversely proportional to the percentage of the protein source. Accordingly, in one embodiment, the collection fluid comprises seminal plasma. In another embodiment, the collection fluid contains seminal plasma in an amount of about 0.5% (v/v) to about 10% (v/v), preferably in an amount of about 4% (v/v) to about 6% (v/v), and more preferably in an amount of about 5% (v/v). In another embodiment, the collection fluid contains a protein source and seminal plasma. In yet another embodiment, the collection fluid comprises seminal plasma and egg yolk, the percentage of both totaling between about 1% (v/v) and about 30% (v/v).

Optionally, the collection fluid may also contain a range of additives that are beneficial to sperm viability or motility. Examples of such additives include an energy source and an antibiotic, each of which is discussed above with respect to collection of the sample cells. Such additives may be added to the collection fluid in accordance therewith.

Accordingly, in a certain embodiment, the collection fluid comprises A composition which regulates oxidation/reduction reactions intracellularly and/or extracellularly, 0.96% Dulbecco's PBS (w/v), 1% (w/v) fructose, 10% (v/v) egg yolk in water, at a pH of about 7.0. In yet another embodiment, the composition which regulates oxidation/reduction reactions intracellularly and/or extracellularly comprises 10 mM pyruvate, 100 µM vitamin K, 1 mM of lipoic acid, or any combination thereof.

Alternatively, and in lieu of the use of a collection fluid, the sorted cells may be collected into a vessel containing or coated with a cryoextender used in the subsequent cryopreservation steps and further described below. Accordingly, in one particular embodiment, the sorted cells are collected into a cryoextender. For example, the cryoextender may comprise water, Triladyle (Minitube, Verona, Wis., comprising glycerol, tris, citric acid, fructose, 5 mg/100 ml tylosin, 25 mg/100 ml gentamycin, 30 mg/100 ml Spectinomycin, and 15 mg/100 ml Lincomycin), egg yolk, and a composition which regulates oxidation/reduction reactions intracellularly and/or extracellularly. In yet another embodiment, the cryoextender comprises 25 g Triladyl®, and 25 g egg yolk per 75 ml of water, and composition which regulates oxidation/reduction reactions intracellularly and/or extracellularly.

It is to be understood that the percent concentrations of protein in the collection fluid disclosed herein are those prior to the addition of the flow sorted cells. The addition of the flow sorted cells may dilute the final concentration of the collection fluid to about 1/20 that of what it was prior to the addition of the flow sorted cells. Therefore, for example, the collection fluid may initially contain about 10% (v/v) egg yolk. After the flow sorted cells are collected in the collection vessel containing the collection fluid, the final concentration of egg yolk will be reduced to about 0.5% (v/v). Alternatively, the addition of the flow sorted cells may dilute the final concentration of the collection fluid to about 1/15 that of what it was prior to the addition of the flow sorted cells. Therefore, for example, the collection fluid may initially contain about 20% (v/v) egg yolk. After the flow sorted cells are collected in the collection vessel containing the collection fluid, the final concentration of egg yolk will be reduced to about 1.3% (v/v).

Cryoextension of the Sorted Cells

Once the sperm have been sorted and collected in the collection vessels, they may be used for inseminating female mammals. This can occur almost immediately, requiring little additional treatment of the sperm. Likewise, the sperm may also be cooled or frozen for use at a later date. In such instances, the sperm may benefit from additional treatment to minimize the impact upon viability or post-thaw motility as a result of cooling and freezing.

Generally, a cryoextender comprises a buffer or buffered solution, a composition which regulates oxidation/reduction reactions intracellularly and/or extracellularly, a protein source, and a cryoprotectant. Examples of buffers and buffered solutions that may be used in the cryoextender are disclosed above with respect to sample collection and extension.

Typically, these buffers will be in a concentration of about 0.001M to about 1.0M and have a pH of about 4.5 to about 8.5, preferably of about 7.0.

If included, a protein source may be added, for example, to provide support to the cells. The protein source may be any protein source that does not interfere with the viability of the sperm cells and is compatible with the particular buffer or buffered solution being used. Examples of common protein sources include milk (including heat homogenized and skim), milk extract, egg yolk, egg yolk extract, soy protein and soy protein extract. Such proteins may be found in a concentration from about 10% (v/v) to about 30% (v/v), preferably from about 10% (v/v) to about 20% (v/v), and more preferably about 20% (v/v). While milk may be used in combination with a buffer or buffered solution, generally milk is used in the absence of the same, as milk is a solution itself that may serve the same purpose of a buffer or buffered solution. In such instances, the cryoextender would contain about 80% (v/v) to about 90% (v/v) milk.

A cryoprotectant is preferably included in the cryoextender to lessen or prevent cold shock or to maintain fertility of the sperm. Numerous cryoprotectants are known in the art. Selection of a cryoprotectant suitable for use with a given extender may vary, and depends upon the species from which the sperm to be frozen were obtained. Examples of suitable cryoprotectants include, for example, glycerol, dimethyl sulfoxide, ethylene glycol, propylene glycol, trehalose, Triladyl® and combinations thereof. If included, generally, these cryoprotectants are present in the cryoextender in an amount of about 1% (v/v) to about 15% (v/v), preferably in an amount of about 5% (v/v) to about 10% (v/v), more preferably in an amount of about 7% (v/v), and most preferably in an amount of about 6% (v/v).

In one particular embodiment, the cryoextender comprises water, Triladyl®, egg yolk, and a composition which regulates oxidation/reduction reactions intracellularly and/or extracellularly. In yet another embodiment, the cryoextender comprises 25 g Triladyl® and 25 g egg yolk per 75 ml of water, and a composition which regulates oxidation/reduction reactions intracellularly and/or extracellularly.

Optionally, the cryoextender may also contain a range of additives that are beneficial to sperm viability or motility and that prevent or lessen the detrimental side effects of cryopreservation. Such additives may include, for example, an energy source or an antibiotic, each of which is discussed above with respect to sample collection and dilution. Such additives may be added to the cryoextender in accordance therewith.

Having described the invention in detail, it will be apparent that modifications and variations are possible without departing the scope of the invention defined in the appended claims.

EXAMPLES

The following non-limiting examples are provided to further illustrate the present invention.

Example 1

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, 1 mL of 150×10$^6$ sperm/ml suspension was prepared by removing an aliquot of the carbonate sperm suspension centrifuging the sperm suspension at 500×g for 5 minutes, removing the supernatant and re-suspending the pellet in 41° C. TCA buffer pH 7.3. An additional 1 mL of 150×10$^6$ sperm/ml was prepared by suspending an aliquot of semen in 41° C. TCA buffer containing 10 mM pyruvate at pH 7.3. To the sperm suspensions, aliquots of a 10 mM Hoechst solution in water were added to yield the dye concentration of 400 µM Hoechst. The sperm suspensions were maintained in a 41° C. water bath for the duration of the staining period. Sperm suspensions were analyzed by removing a 50 µL aliquot from the staining sperm suspension, adding 200 µL of the same buffer at the same temperature and analyzing by IVOS to measure % progressive motility (% Prog Mot). Results of the IVOS analysis are summarized in FIG. 1.

Example 2

Figure 2:
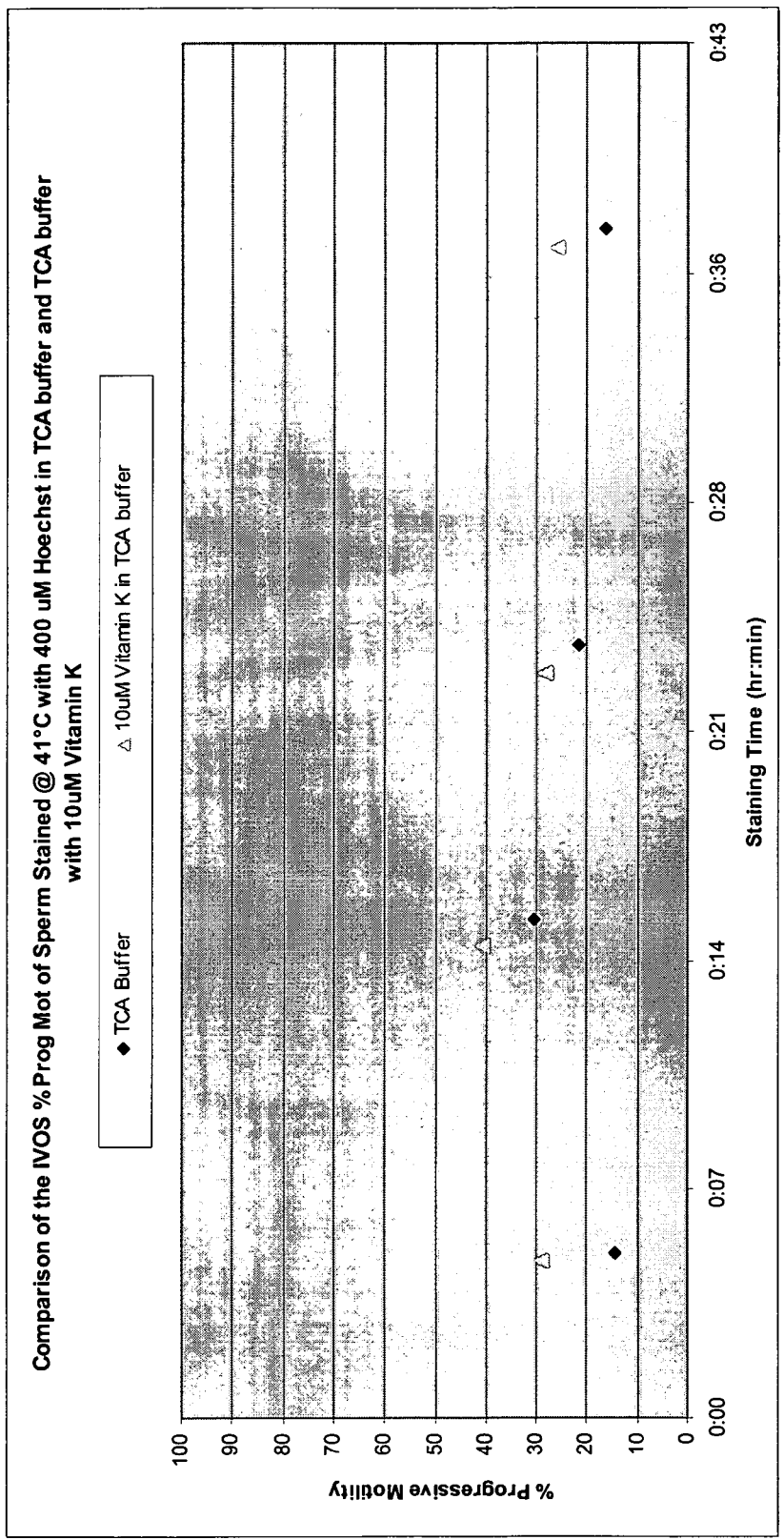
FIG. 2 graphically depicts the results of the study carried out in Example 2 wherein percent progressive motility of sperm is measured for sperm stained with 400 μM Hoechst 33342 dye at 41° C. in either a TCA buffer or a TCA buffer containing 10 μM vitamin K.

Sperm samples were obtained and prepared in the same manner as in Example 1 with the following exception. The buffer used to suspend the sperm for staining and IVOS analysis were TCA and TCA containing 10 uM Vitamin K. Results of the IVOS analysis are summarized in FIG. 2.

Example 3

Figure 3:
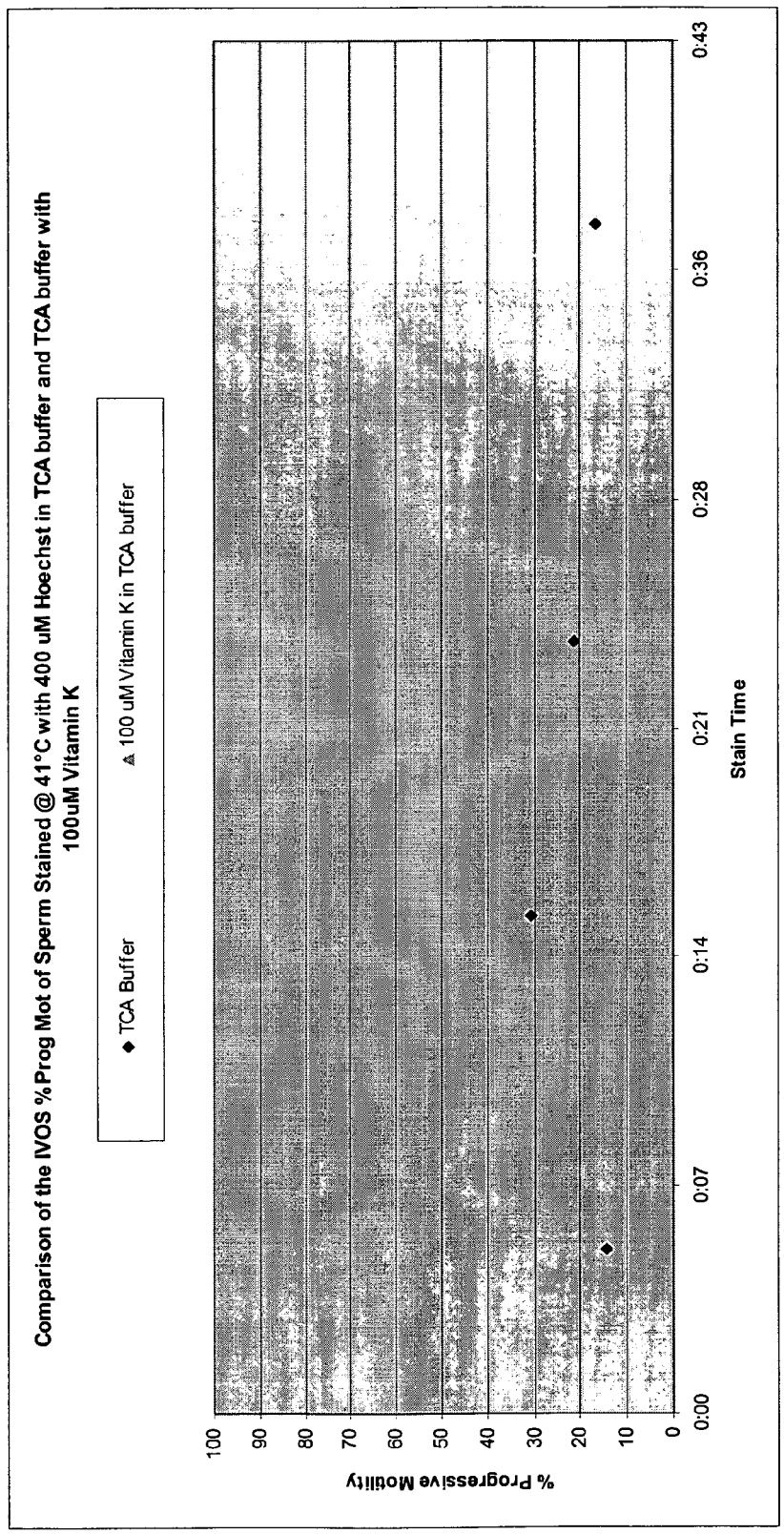
FIG. 3 graphically depicts the results of the study carried out in Example 3 wherein percent progressive motility of sperm is measured for sperm stained with 400 μM Hoechst 33342 dye at 41° C. in either a TCA buffer or a TCA buffer containing 100 μM vitamin K.

Sperm samples were obtained and prepared in the same manner as in Example 1 with the following exception. The buffer used to suspend the sperm for staining and IVOS analysis were TCA and TCA containing 100 uM Vitamin K. Results of the IVOS analysis are summarized in FIG. 3.

Example 4

Figure 4:
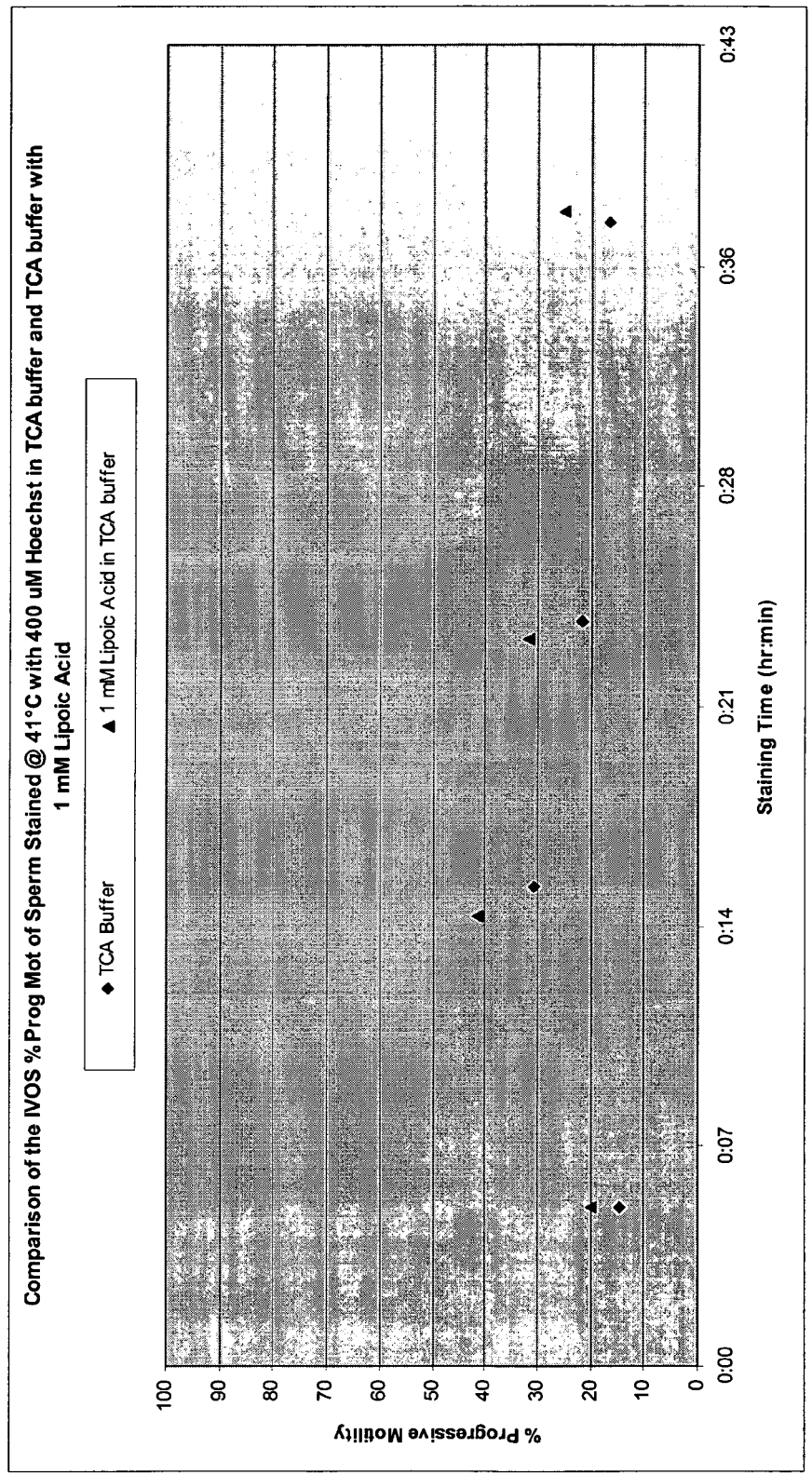
FIG. 4 graphically depicts the results of the study carried out in Example 4 wherein percent progressive motility of sperm is measured for sperm stained with 400 μM Hoechst 33342 dye at 41° C. in either a TCA buffer or a TCA buffer containing 1 mM lipoic acid.

Sperm samples were obtained and prepared in the same manner as in Example 1 with the following exception. The buffers used to suspend the sperm for staining and IVOS analysis were TCA and TCA containing 1 mM Lipoic Acid. Results of the IVOS analysis are summarized in FIG. 4.

Example 5

Figure 5:
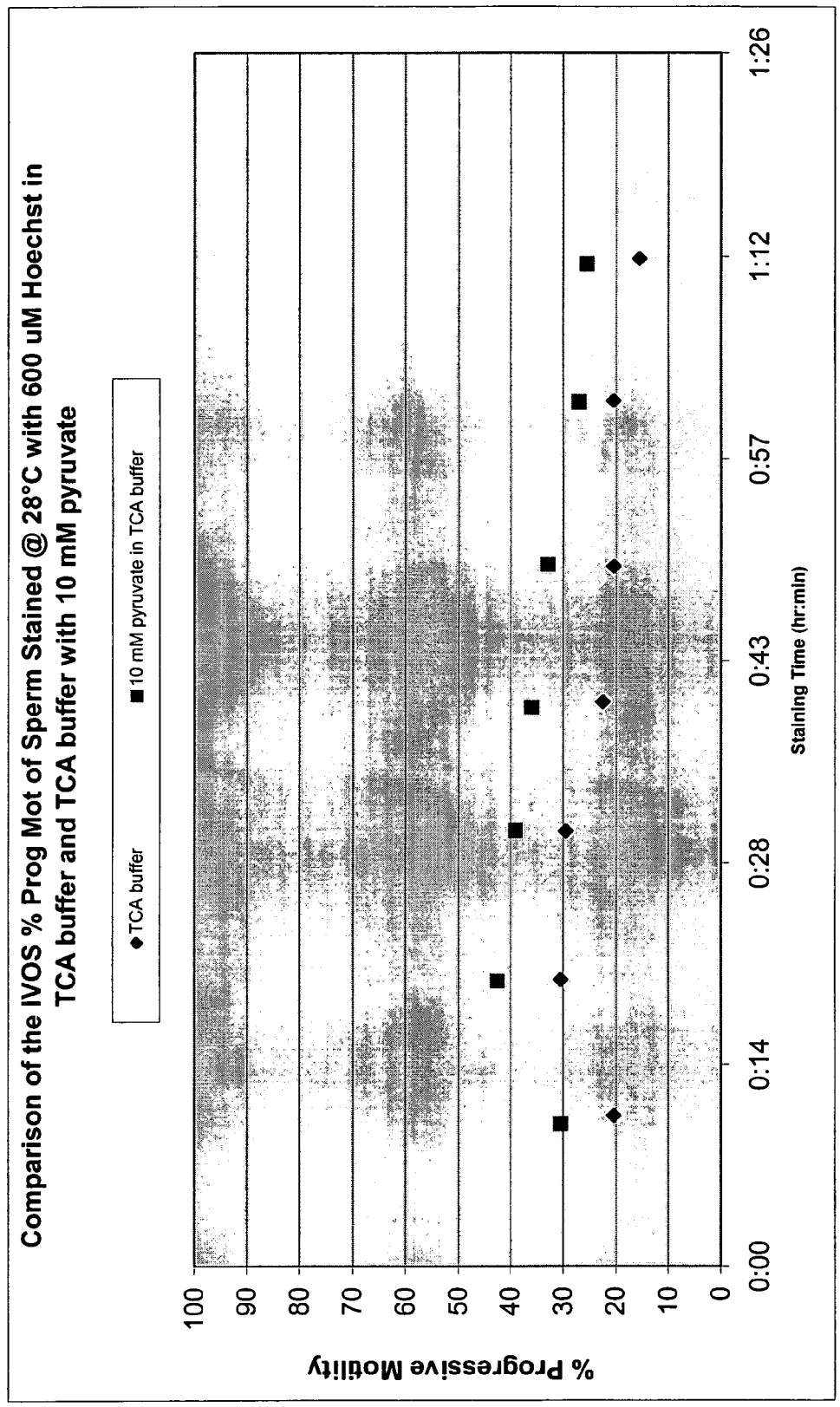
FIG. 5 graphically depicts the results of the study carried out in Example 5 wherein percent progressive motility of sperm is measured for sperm stained with 600 μM Hoechst 33342 dye at 28° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, 1 mL of 150×10$^6$ sperm/ml suspension was prepared by centrifuging the sperm suspension at 500×g for 5 minutes, removing the supernatant and re-suspending the pellet in 28° C. TCA buffer pH 7.3. An additional 1 mL of 150×10$^6$ sperm/ml was prepared by suspending an aliquot of semen in 28° C. TCA buffer containing 10 mM pyruvate at pH 7.3. To the sperm suspensions, aliquots of a 10 mM Hoechst solution in water were added to yield the dye concentration of 600 µM Hoechst. The sperm suspensions were maintained in 28° C. water bath for the duration of the staining period. Sperm suspensions were analyzed by removing a 50 µL aliquot from the staining sperm suspension, adding 200 µL of the same buffer at the same temperature and analyzing by IVOS to measure percent progressive motility (% Prog Mot). Results of the IVOS analysis are summarized in FIG. 5.

Example 6

Figure 6:
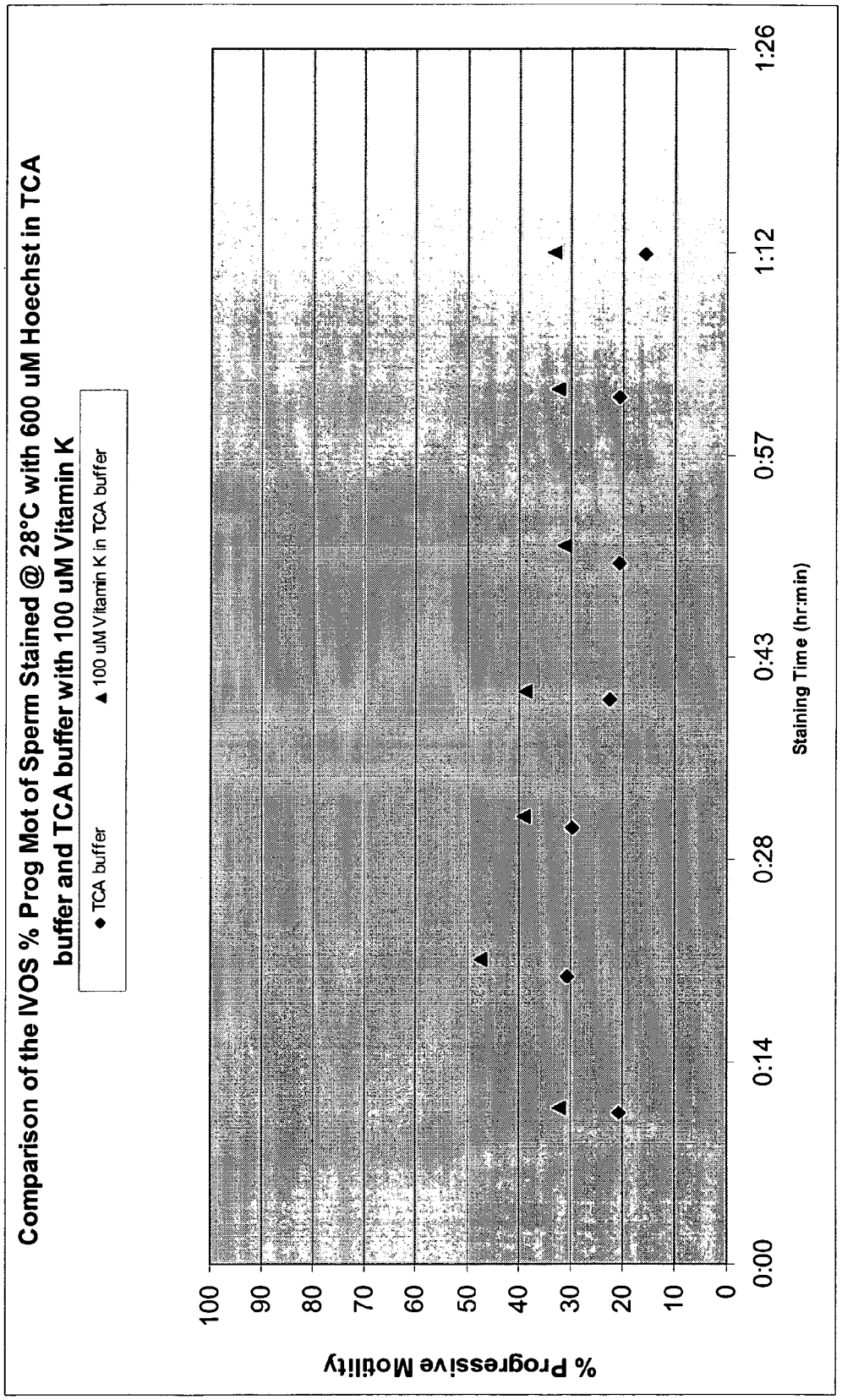
FIG. 6 graphically depicts the results of the study carried out in Example 6 wherein percent progressive motility of sperm is measured for sperm stained with 600 μM Hoechst 33342 dye at 28° C. in either a TCA buffer or a TCA buffer containing 100 μM vitamin K.

Sperm samples were obtained and prepared in the same manner as in Example 5 with the following exception. The buffer used to suspend the sperm for staining and IVOS analysis were TCA and TCA containing 100 uM Vitamin K. Results of the IVOS analysis are summarized in FIG. 6.

Example 7

Figure 7:
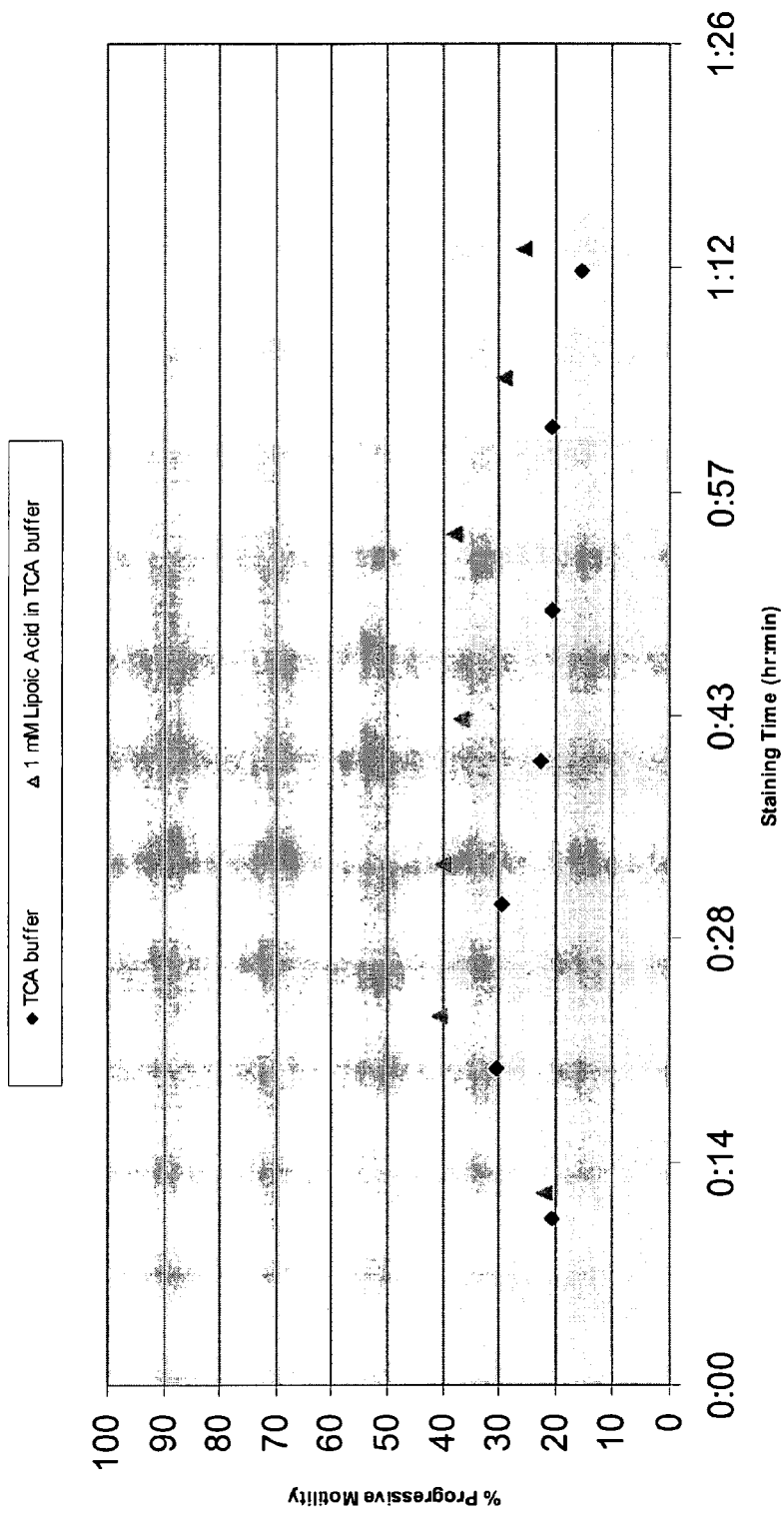
FIG. 7 graphically depicts the results of the study carried out in Example 7 wherein percent progressive motility of sperm is measured for sperm stained with 600 μM Hoechst 33342 dye at 28° C. in either a TCA buffer or a TCA buffer containing 1 mM lipoic acid.

Sperm samples were obtained and prepared in the same manner as in Example 5 with the following exception. The buffer used to suspend the sperm for staining and IVOS analysis were TCA and TCA containing 1 mM Lipoic Acid. Results of the IVOS analysis are summarized in FIG. 7.

Example 8

Figure 8:
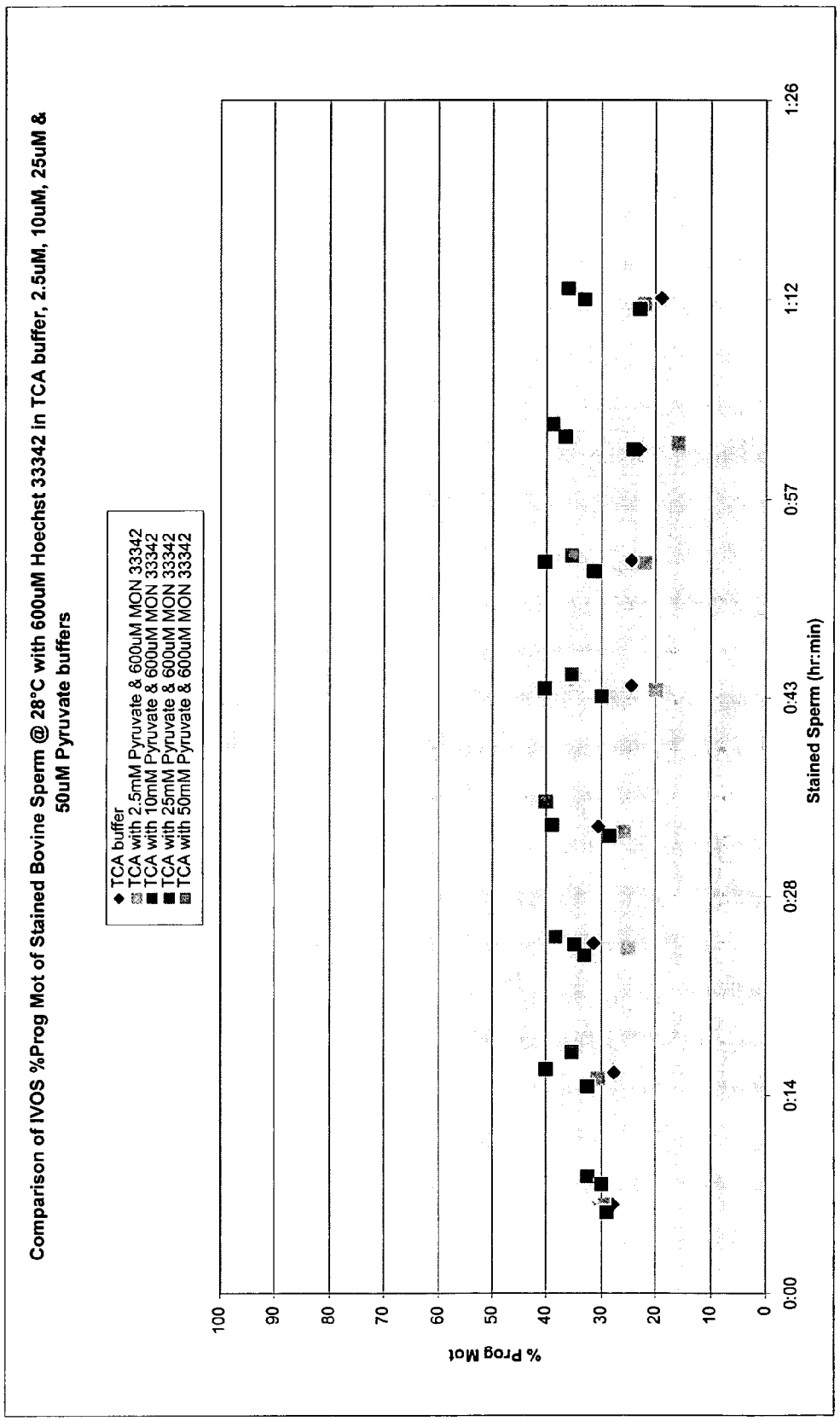
FIG. 8 graphically depicts the results of the study carried out in Example 8 wherein percent progressive motility of sperm is measured for sperm stained with 600 μM Hoechst 33342 dye at 28° C. in a TCA buffer, a TCA buffer containing 2.5 mM pyruvate, a TCA buffer containing 10 mM pyruvate, a TCA buffer containing 25 mM pyruvate, and a TCA buffer containing 50 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, 1 mL of $150 \times 10^6$ sperm/ml suspensions were prepared by removing an aliquots of the carbonate sperm suspension, centrifuging the sperm suspension at 500×g for 5 minutes, removing the supernatant and re-suspending the pellet in 1 ml TCA buffer or in 1 ml TCA buffer with 2.5 mM, 10 mM, 25 mM, or 50 mM pyruvate. To the samples was added MON33342 solution to yield the final dye concentrations of 600 μM. The suspensions were incubated in a 28° C. water bath. Stained sperm suspensions were analyzed by removing a 50 μL aliquot from the staining sperm suspension, adding 200 μL of the same buffer at the same temperature and analyzing by IVOS to measure percent progressive motility (% Prog Mot). IVOS results for % Prog Mot are shown in FIGS. 8.

Example 9

Figure 9:
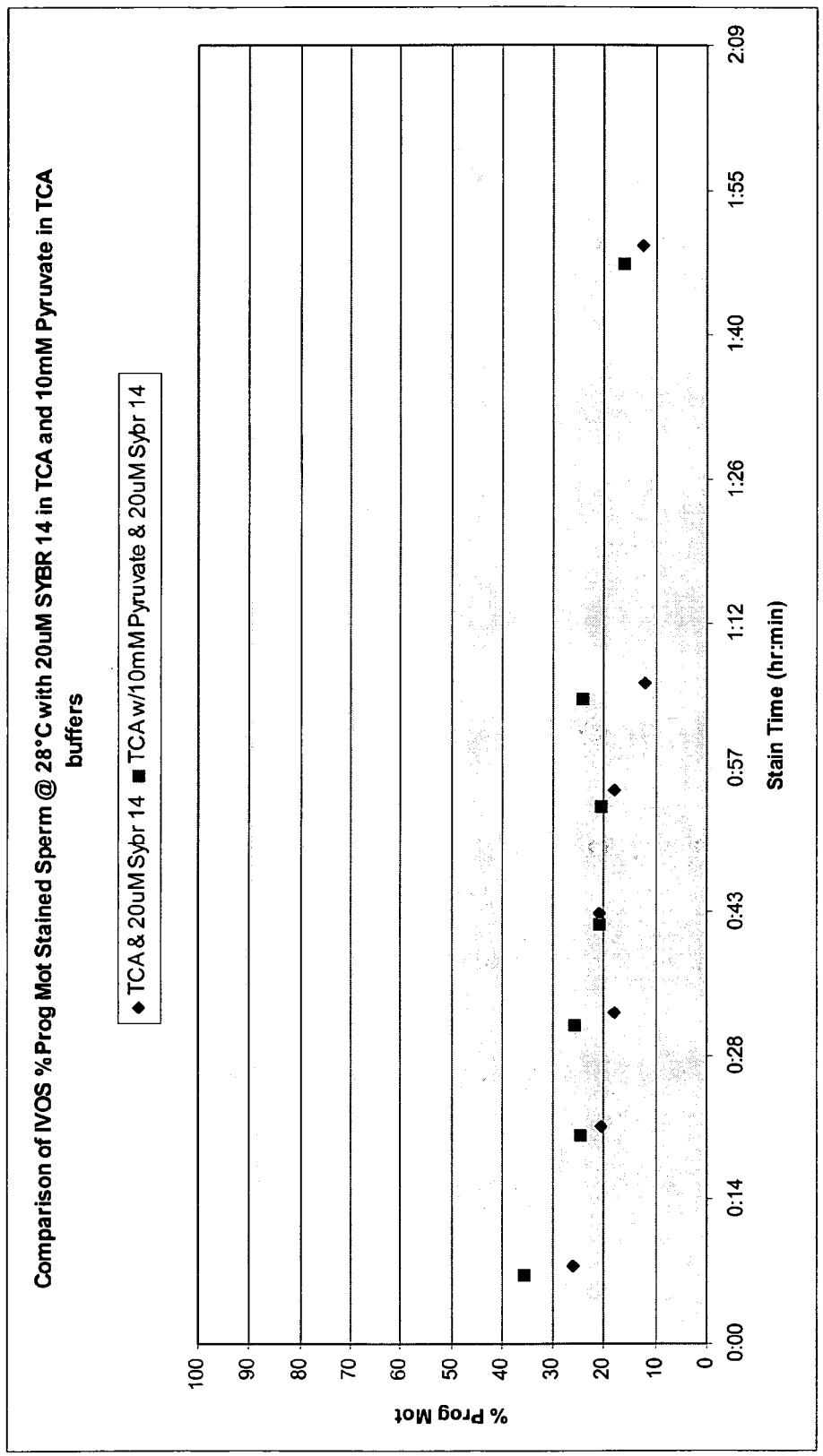
FIG. 9 graphically depicts the results of the study carried out in Example 9 wherein percent progressive motility of sperm is measured for sperm stained with 20 μM SYBR-14 dye at 28° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, 1 mL of $150 \times 10^6$ sperm/ml suspension in TCA buffer was prepared by removing an aliquot of the carbonate sperm suspension, centrifuging the sperm suspension at 500×g for 5 minutes, removing the supernatant and re-suspending the pellet in 1 mL TCA buffer. 1 ml of $150 \times 10^6$ sperm/ml suspension in 10 mM pyruvate in TCA was prepared by removing an aliquot of the carbonate sperm suspension, centrifuging the sperm suspension at 500×g for 5 minutes, removing the supernatant and re-suspending the pellet in 1 ml of 10 mM pyruvate TCA buffer. To samples was added SYBR 14 dye solution to yield the final dye concentrations of 20 μM The suspensions were incubated in a 28° C. water bath. Sperm suspensions were analyzed by removing a 50 μL aliquot from the staining sperm suspension, adding 200 μL of the same buffer at the same temperature and analyzing by IVOS to measure percent progressive motility (% Prog Mot). IVOS results for % Prog Mot are shown in FIGS. 9.

Example 10

Figure 10:
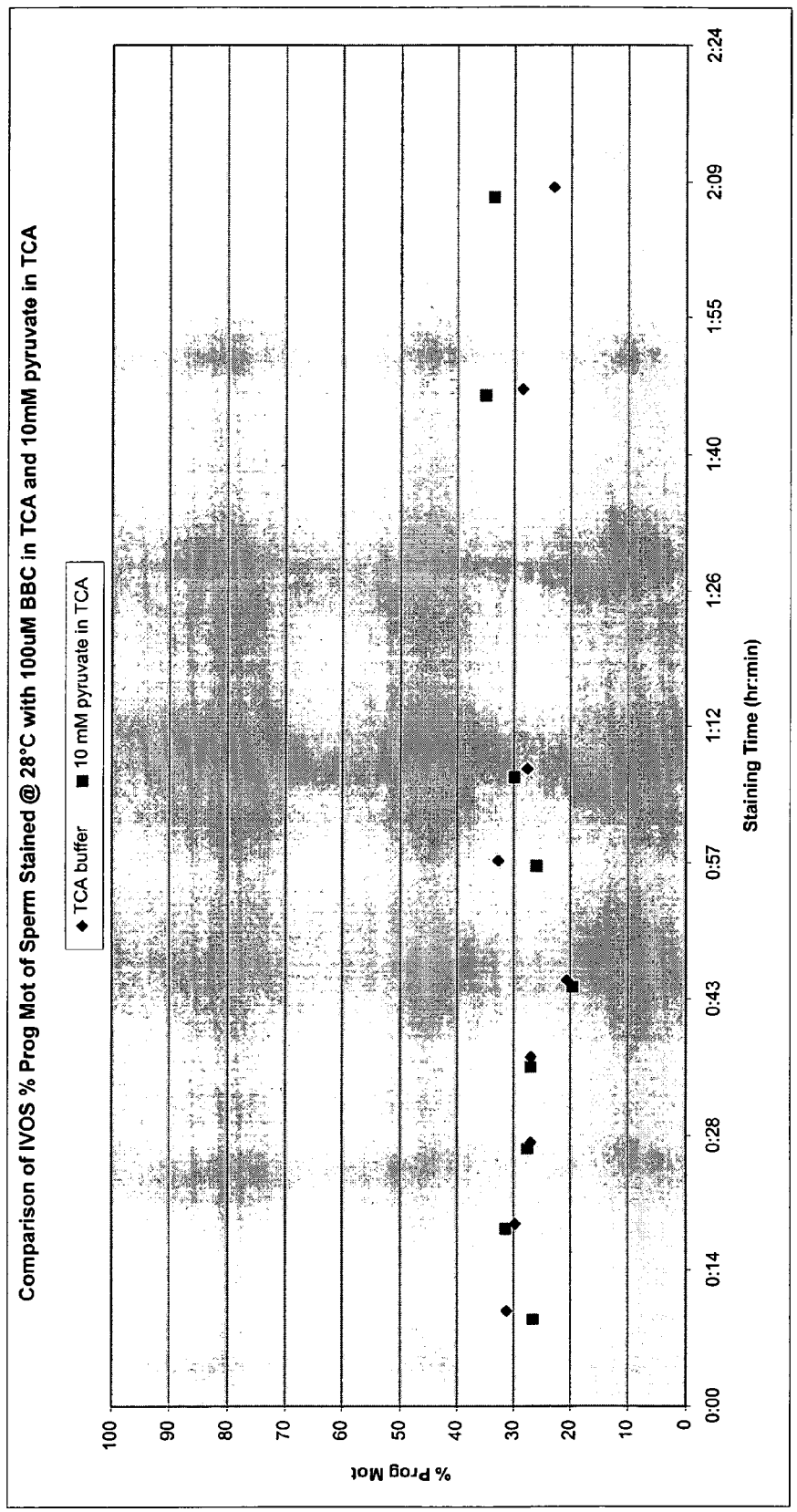
FIG. 10 graphically depicts the results of the study carried out in Example 10 wherein percent progressive motility of sperm is measured for sperm stained with 100 μM BBC dye at 28° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, 1 mL of $150 \times 10^6$ sperm/ml suspension in TCA buffer was prepared by removing an aliquot of the carbonate sperm suspension, centrifuging the sperm suspension at 500×g for 5 minutes, removing the supernatant and re-suspending the pellet in 1 mL TCA buffer. 1 ml of $150 \times 10^6$ sperm/ml suspension in 10 mM pyruvate in TCA was prepared by removing an aliquot of the carbonate sperm suspension, centrifuging the sperm suspension at 500×g for 5 minutes, removing the supernatant and re-suspending the pellet in 1 ml of 10 mM pyruvate TCA buffer. To the samples was added BBC solution to yield the final dye concentrations of 100 μM. The suspensions were incubated in a 28° C. water bath. Stained sperm suspensions were analyzed by removing a 50 μL aliquot from the staining sperm suspension, adding 200 μL of the same buffer at the same temperature and analyzing by IVOS to measure percent progressive motility (% Prog Mot). IVOS results for % Prog Mot are shown in FIG. 10.

Example 11

Figure 11:
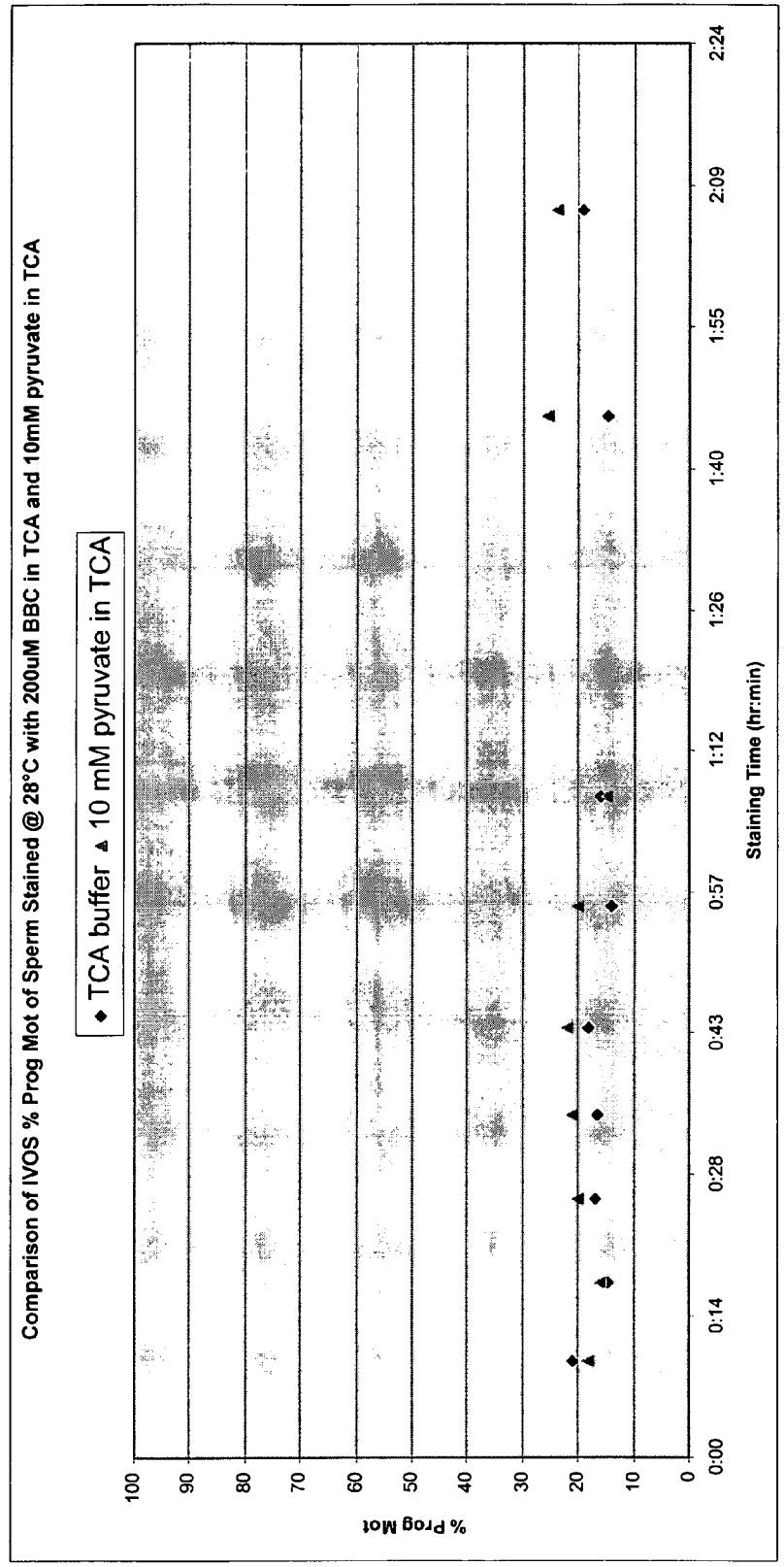
FIG. 11 graphically depicts the results of the study carried out in Example 11 wherein percent progressive motility of sperm is measured for sperm stained with 200 μM BBC dye at 28° C. in either a TCA buffer or a TCA buffer containing 10 mM pyruvate.

Sperm samples were obtained and prepared in the same manner as in Example 10 with the following exception. The staining concentration was 200 uM BBC. Results of the IVOS analysis are summarized in FIG. 11.

Example 12

Bull semen was collected from a sexually mature bull using an artificial vagina and transported at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, several tubes of $150 \times 10^6$ sperm/ml suspensions were prepared by suspending semen in a TCA buffer or a carbonate-based inhibitor. Table II. below illustrates the compositions and staining conditions used.

TABLE II

| Sample Name | Composition | pH | Conc. (uM) Hoechst | Temperature (° C.) |
| --- | --- | --- | --- | --- |
| 10 mM pyr TCA | 10 mM pyruvate in TCA | 7.3 | 600 μM | 28° C. |
| 10 mM pyr $CO_2$ | 10 mM pyruvate in TCA blanket with $CO_2$ balloon | 7.3 | 600 μM | 28° C. |
| Carbonate 6.2 | Carbonate based inhibitor, pH 6.2 | 6.2 | 600 μM | 28° C. |
| Carbonate 7.3 | Carbonate based inhibitor, pH 7.3 | 7.3 | 600 μM | 28° C. |

Figure 12:
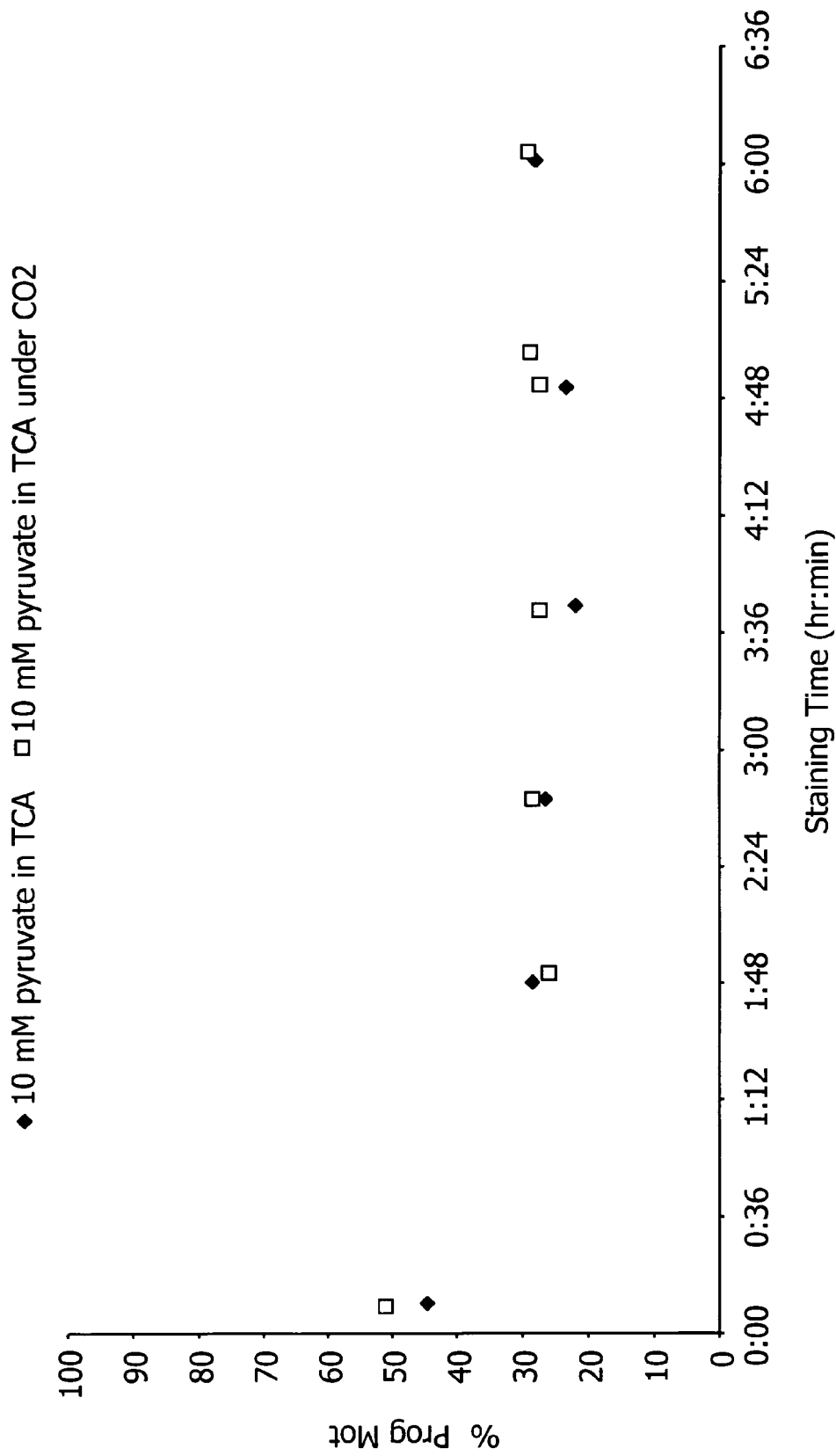
FIG. 12 graphically depicts the results of the study carried out in Example 12 wherein percent progressive motility of sperm cells is measured for sperm cells stained with 600 μM Hoechst 33342 dye at 28° C. in TCA containing 10 mM pyruvate or in carbon dioxide-blanketed TCA containing 10 mM pyruvate.
Figure 13:
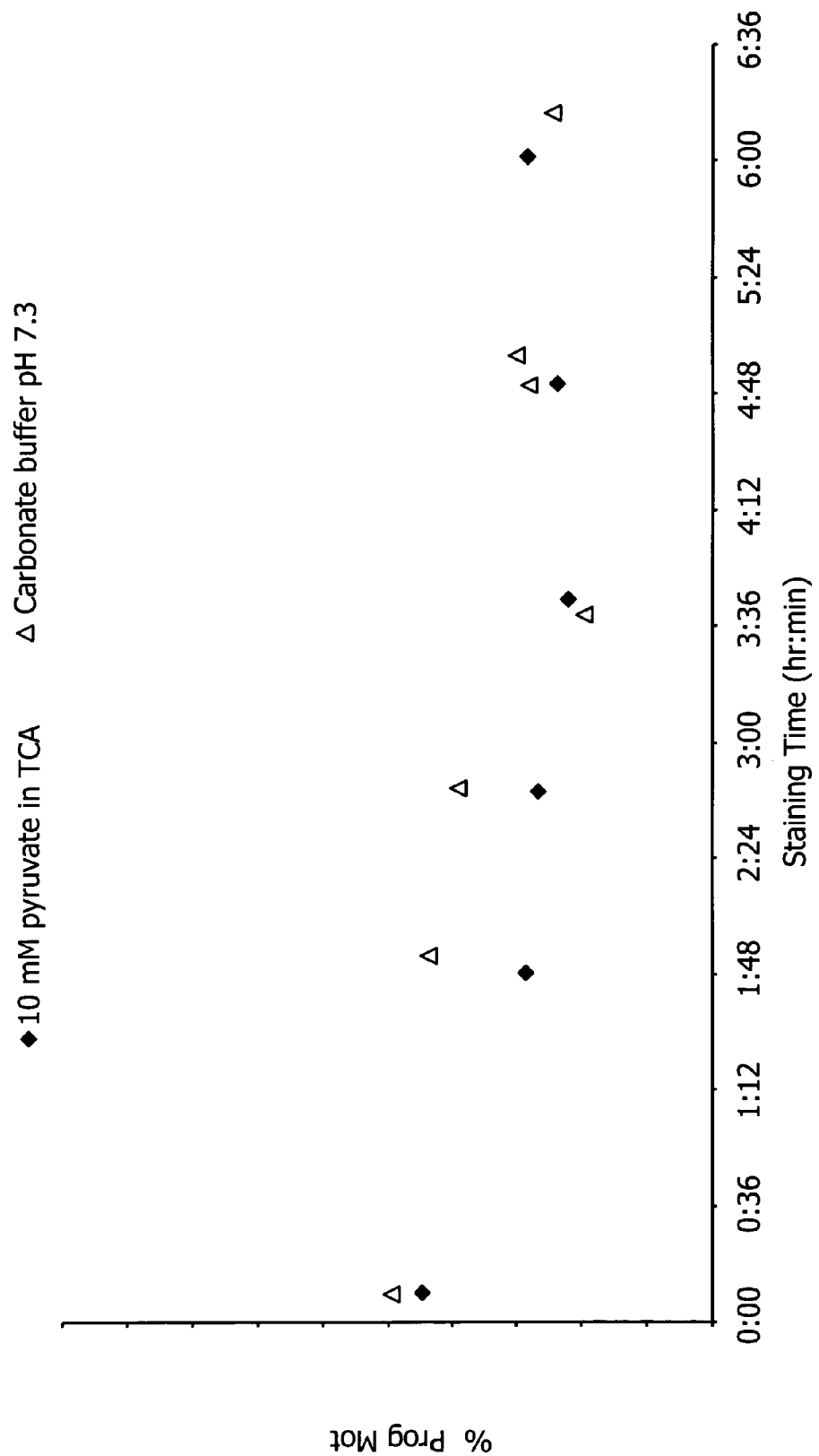
FIG. 13 graphically depicts the results of the study carried out in Example 12 wherein percent progressive motility of sperm cells is measured for sperm cells stained with 600 μM Hoechst 33342 dye at 28° C. in TCA containing 10 mM pyruvate or a carbonate-based inhibitory buffer at pH 7.3.
Figure 14:
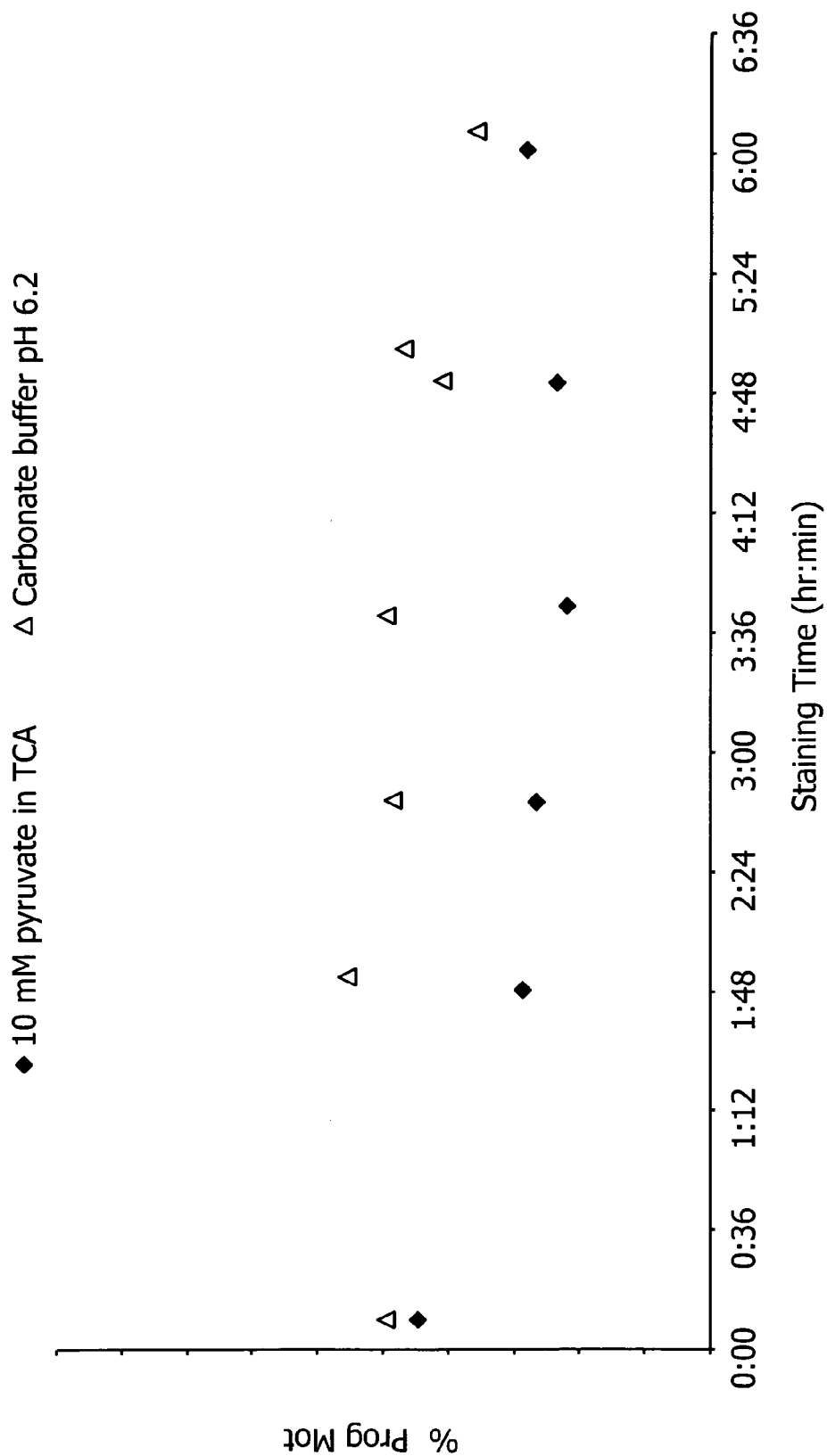
FIG. 14 graphically depicts the results of the study carried out in Example 12 wherein percent progressive motility of sperm cells is measured for sperm cells stained with 600 μM Hoechst 33342 dye at 28° C. in TCA containing 10 mM pyruvate or a carbonate-based inhibitor at pH 6.2.

To the sperm suspensions, aliquots of a 10 mM Hoechst solution in water were added to yield a concentration of 600 µM Hoechst. The sperm suspensions were maintained in a 28° C. water bath for the duration of the staining period (approximately 1 hour). Sperm suspensions were analyzed by removing a 50 µL aliquot from the stained sperm suspension, adding 200 µL of 25° C. 10 mM pyruvate in TCA at pH 7.3 to initiate the reversal of the quiescence, allowing at least a five minute equilibration period, and analyzing by IVOS to measure percent progressive motility (% Prog. Mot.). Comparisons of the IVOS percent progressive motilities are seen in FIGS. 12-14.

Example 13

Bull semen was collected from a sexually mature bull using an artificial vagina and transported at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology,* 49(4): 871-9 (March 1998)). Based on the semen concentration, several tubes of $450 \times 10^6$ sperm/ml suspensions were prepared by suspending semen in either a TCA buffer or a carbonate based inhibitor. Table III. below illustrates the compositions and staining conditions used.

TABLE III

| Sample Name | Composition | pH | Conc. (uM) Hoechst | Temperature (° C.) |
|---|---|---|---|---|
| 10 mM pyr TCA | 10 mM pyruvate in TCA | 7.3 | 1000 µM | 28° C. |
| Carbonate 6.2 | Carbonate based inhibitor, pH 6.2 | 6.2 | 1000 µM | 28° C. |
| Carbonate 7.3 | Carbonate based inhibitor, pH 7.3 | 7.3 | 1000 µM | 28° C. |

Figure 15:
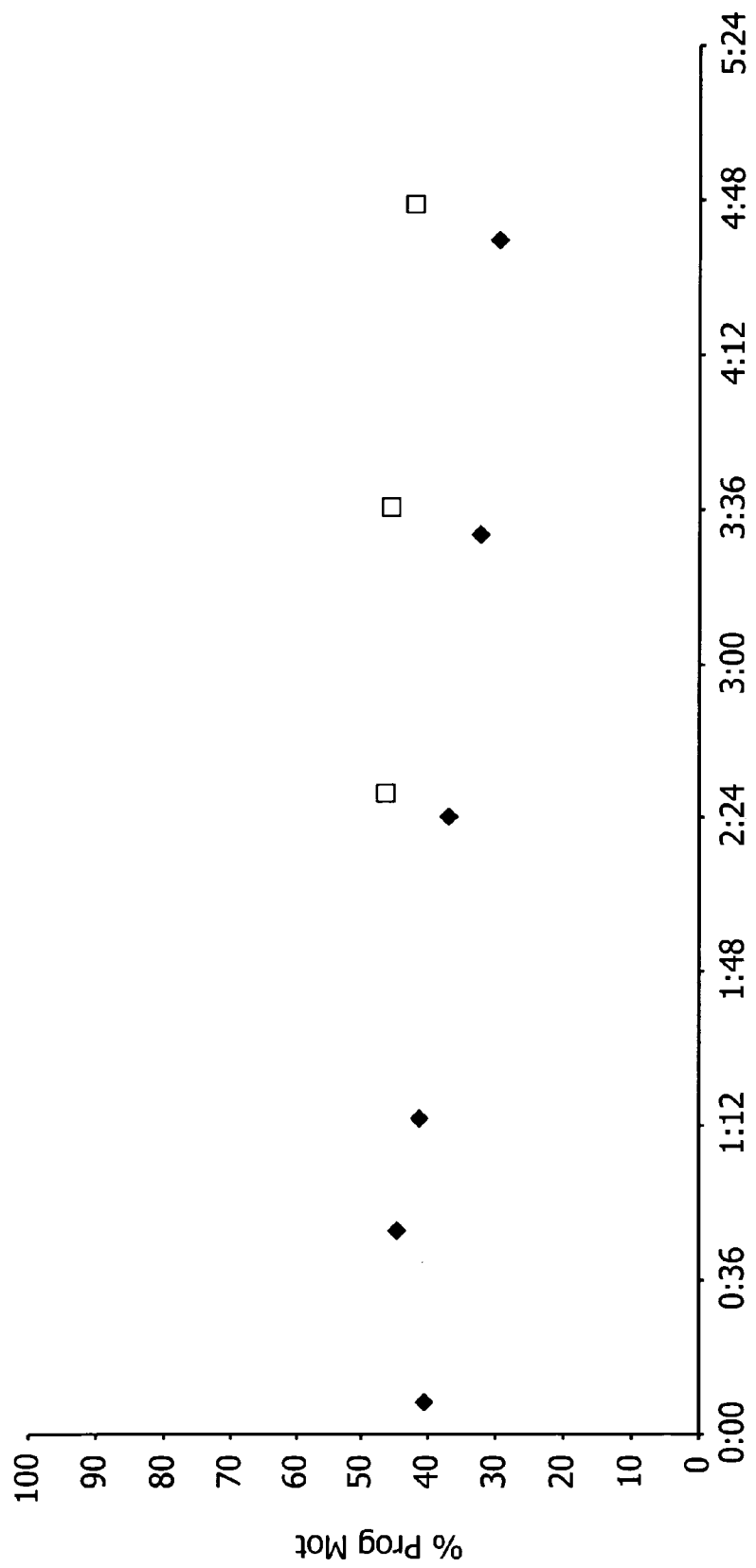
FIG. 15 graphically depicts the results of the study carried out in Example 13 wherein percent progressive motility of sperm cells is measured for sperm cells stained with 1000 μM Hoechst 33342 dye at 28° C. in TCA containing 10 mM pyruvate and then diluted 1 to 3 with either TCA containing 10 mM pyruvate or a carbonate-based inhibitor at pH 6.2.
Figure 16:
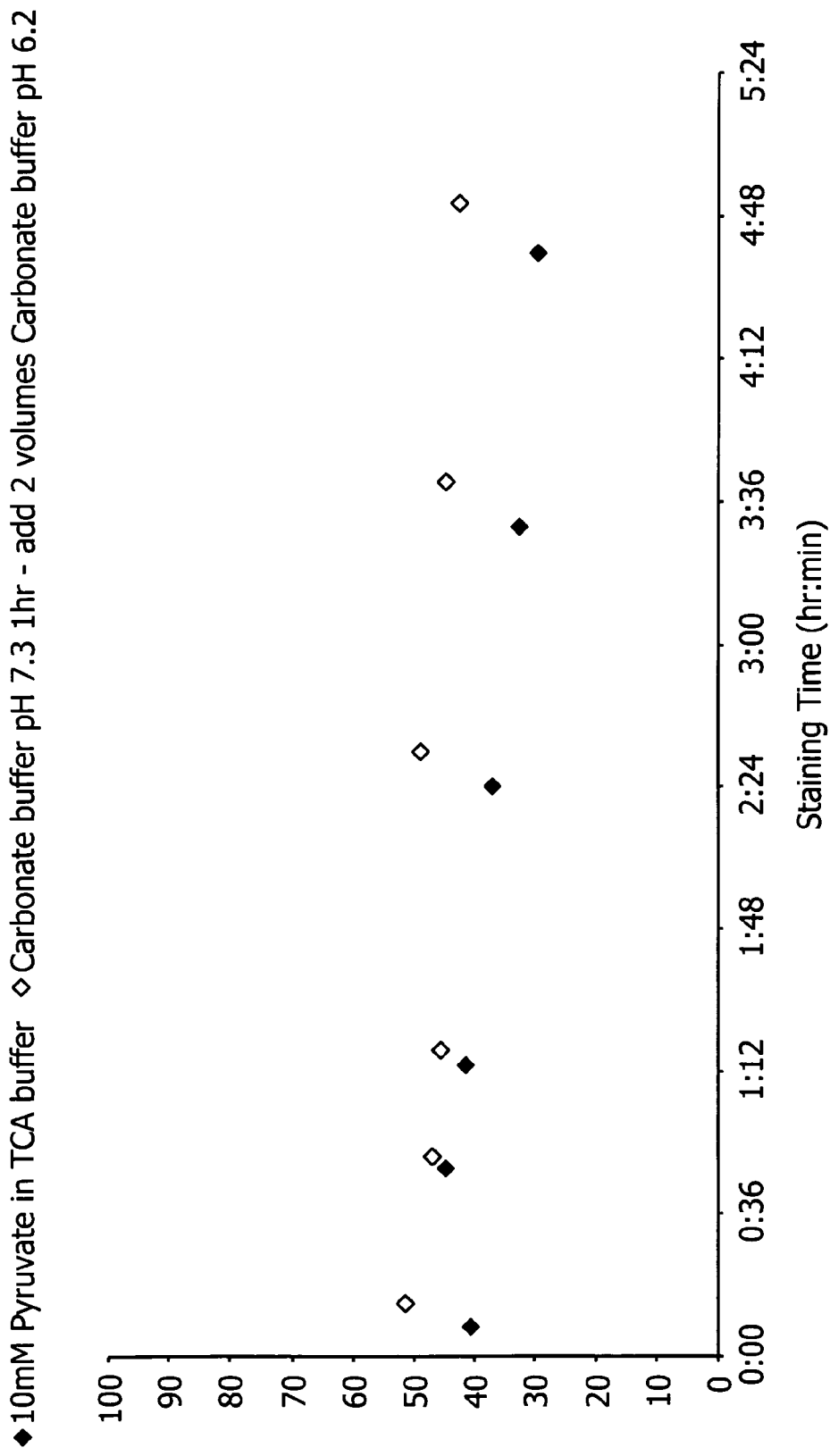
FIG. 16 graphically depicts the results of the study carried out in Example 13 wherein percent progressive motility of sperm cells is measured for sperm cells stained with 1000 μM Hoechst 33342 dye at 28° C. in (1) TCA containing 10 mM pyruvate and diluted 1 to 3 with the same or (2) a carbonate-based buffer at pH 7.3 and diluted 1 to 3 with carbonate-based inhibitor at pH 6.2.
Figure 17:
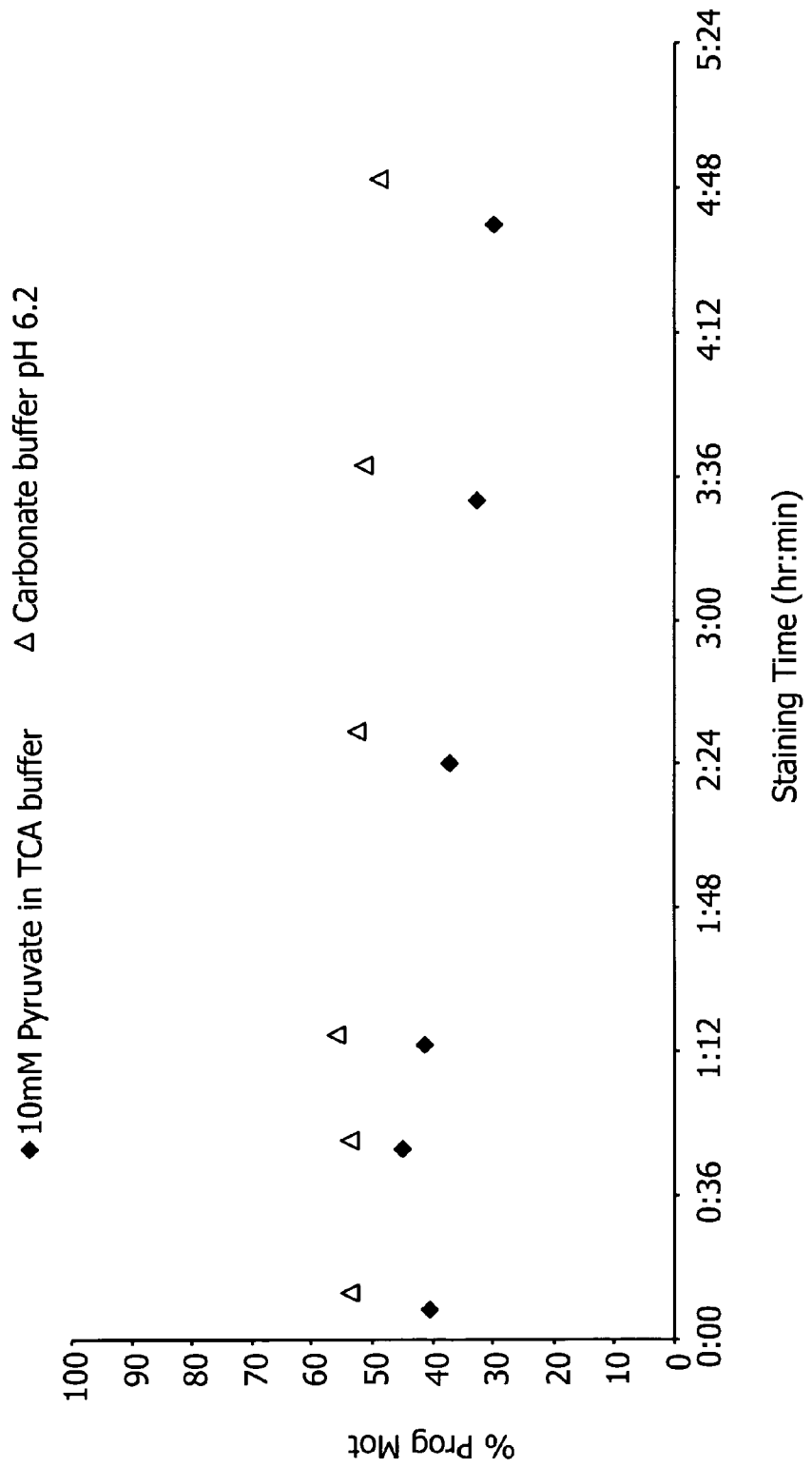
FIG. 17 graphically depicts the results of the study carried out in Example 13 wherein percent progressive motility of sperm cells is measured for sperm cells stained with 1000 μM Hoechst 33342 dye at 28° C. in TCA containing 10 mM pyruvate or a carbonate-based inhibitor at pH 6.2.

To the sperm suspensions, aliquots of a 10 mM Hoechst solution in water were added to yield a concentration of 1000 µM Hoechst. The sperm suspensions were maintained in a 28° C. water bath for 1 hour, and were then diluted to $150 \times 10^6$ sperm/ml with 10 mM pyruvate in TCA or a carbonate-based inhibitor at a pH 6.2 as specifically indicated in each figure to dilute to a concentration typical for sorting. Sperm suspensions were analyzed by removing a 50 µL aliquot from the stained and diluted sperm suspension at the time period designated within each figure and adding 200 µL of 25° C. 10 mM pyruvate in TCA at pH 7.3 to initiate the reversal of the quiescence, allowing at least a five minute equilibration period, and analyzing the aliquot by IVOS to measure the percent progressive motility. Comparisons of the IVOS percent progressive motilities are seen in FIGS. 15-17.

Example 14

Bull semen was collected from a sexually mature bull using an artificial vagina and transported at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology,* 49(4): 871-9 (March 1998)). Based on the semen concentration, several tubes of $450 \times 10^6$ sperm/ml suspensions were prepared by suspending semen in either a TCA buffer or a carbonate based inhibitor. Table IV. below illustrates the compositions and staining conditions used.

TABLE IV

| Sample Name | Buffer | pH | Conc (uM) Hoechst | Temperature (° C.) |
|---|---|---|---|---|
| 10 mM pyr TCA | 10 mM pyruvate in TCA | 7.3 | 300 µM | 41° C. |
| Carbonate 6.2 | Carbonate based inhibitor, pH 6.2 | 6.2 | 300 µM | 41° C. |
| Carbonate 7.3 | Carbonate based inhibitor, pH 7.3 | 7.3 | 300 µM | 41° C. |

Figure 18:
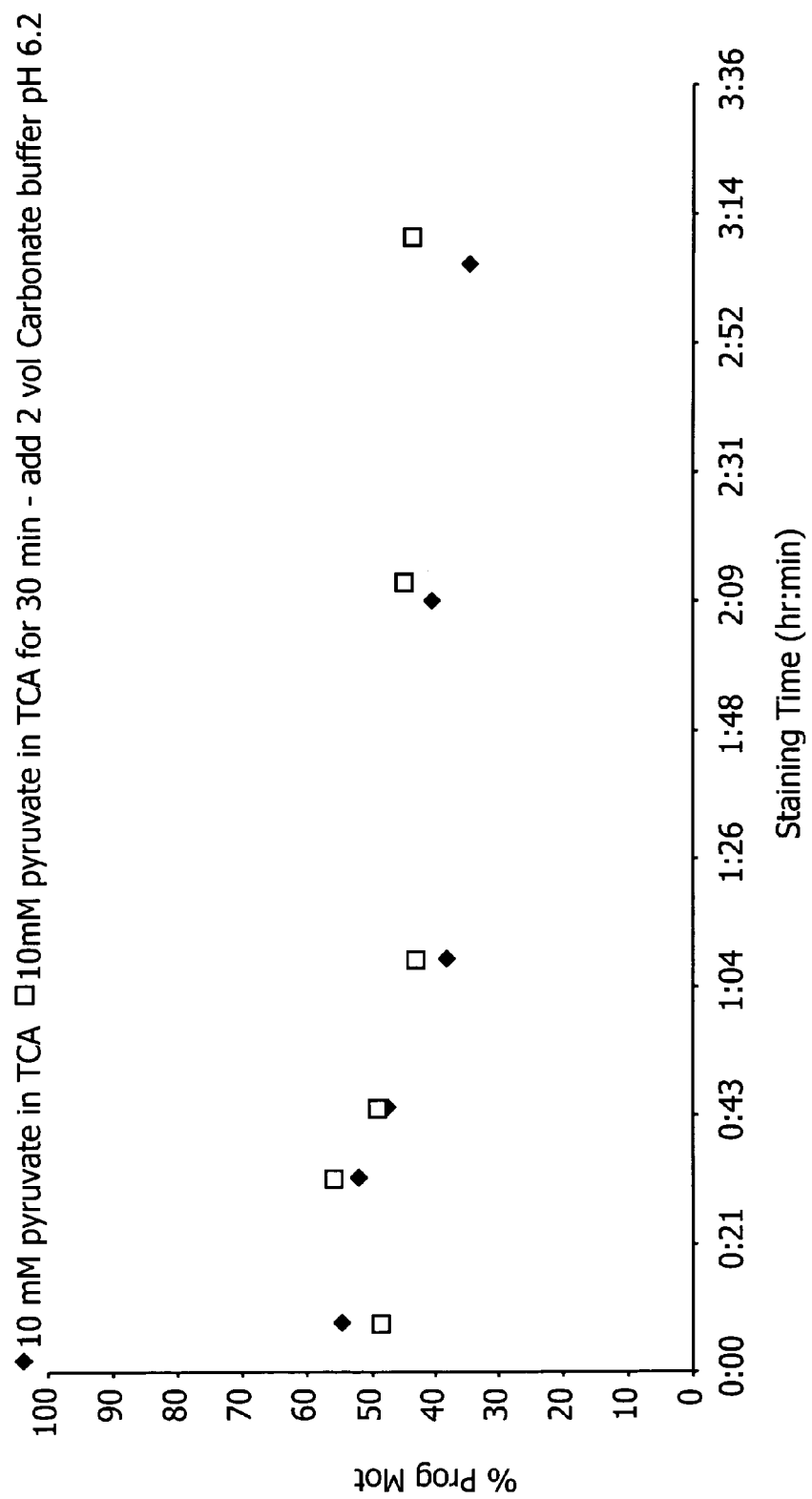
FIG. 18 graphically depicts the results of the study carried out in Example 14 wherein percent progressive motility of sperm cells is measured for sperm cells stained with 300 μM Hoechst 33342 dye at 41° C. in TCA containing 10 mM pyruvate and then diluted 1 to 3 with either TCA containing 10 mM pyruvate or a carbonate-based inhibitor at pH 6.2.
Figure 19:
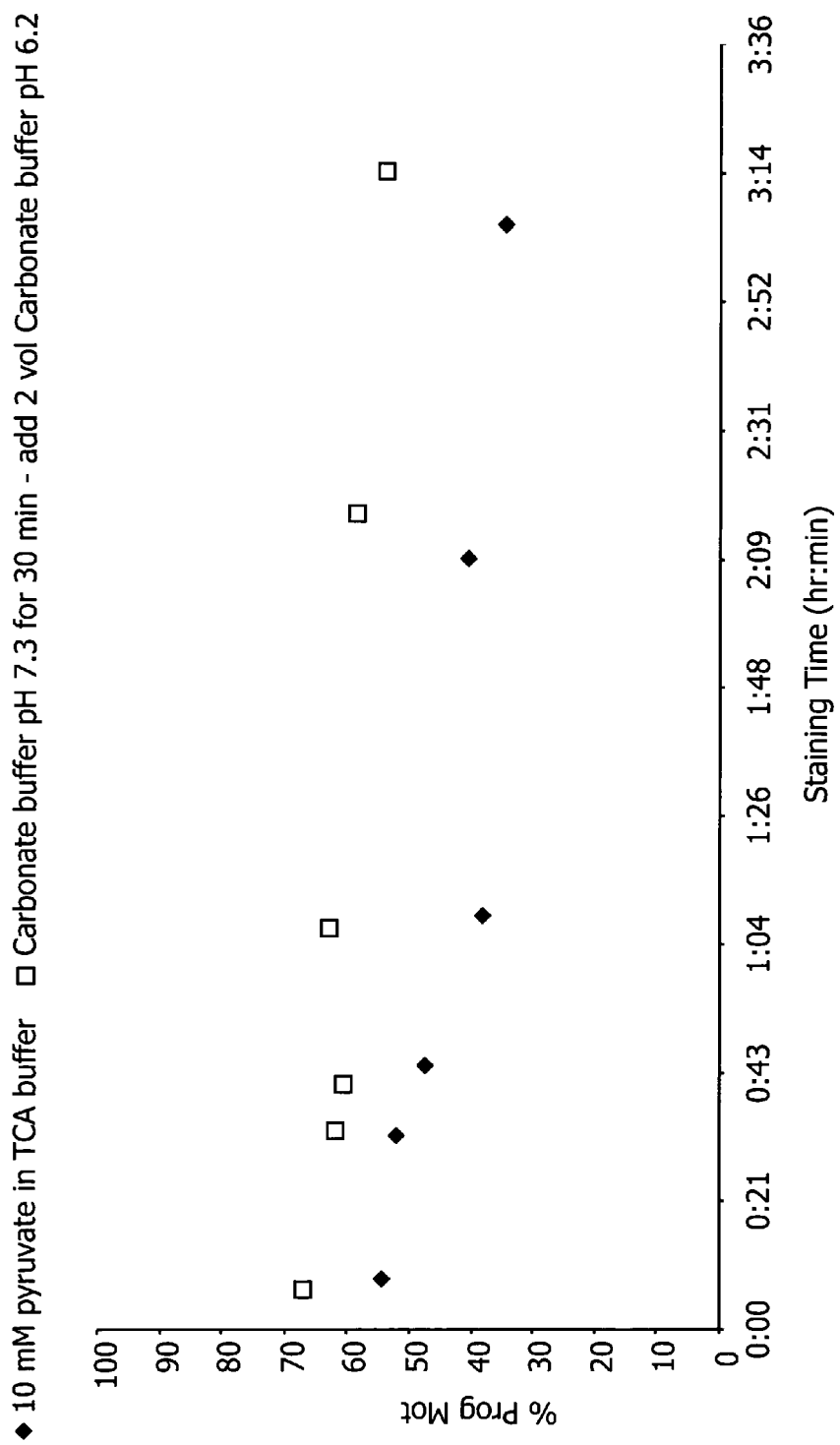
FIG. 19 graphically depicts the results of the study carried out in Example 14 wherein percent progressive motility of sperm cells is measured for sperm cells stained with 300 μM Hoechst 33342 dye at 41° C. in (1) TCA containing 10 mM pyruvate and diluted 1 to 3 with the same or (2) a carbonate-based buffer at pH 7.3 and diluted 1 to 3 with carbonate-based inhibitor at pH 6.2.
Figure 20:
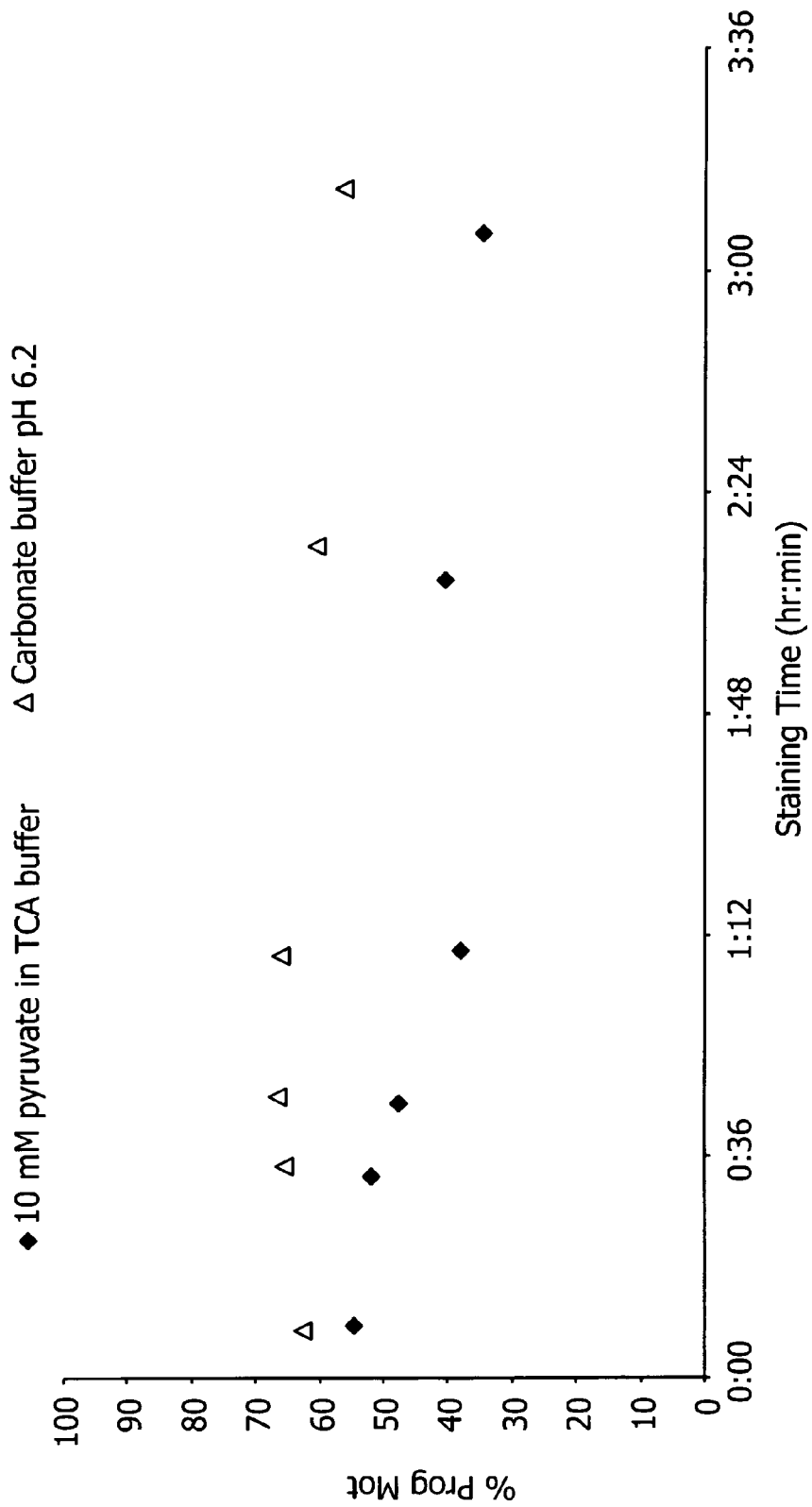
FIG. 20 graphically depicts the results of the study carried out in Example 14 wherein percent progressive motility of sperm cells is measured for sperm cells stained with 300 μM Hoechst 33342 dye at 41° C. in TCA containing 10 mM pyruvate or a carbonate-based inhibitor at pH 6.2.

To the sperm suspensions, aliquots of a 10 mM Hoechst solution in water were added to yield a concentration of 300 µM Hoechst. The sperm suspensions were maintained in a 41° C. water bath for 30 minutes, and then diluted to $150 \times 10^6$ sperm/ml with 10 mM pyruvate in TCA or a carbonate-based inhibitor at pH 6.2 as specifically indicated in each figure to dilute to a concentration typical for sorting. Sperm suspensions were analyzed by removing a 50 µL aliquot from the stained and diluted sperm suspension at the time period designated within each figure and adding 200 µL of 25° C. 10 mM pyruvate in TCA at pH 7.3 to initiate the reversal of the quiescence, allowing at least a five minute equilibration period, and analyzing by IVOS to measure the percent progressive motility. Comparisons of the IVOS percent progressive motilities are seen in FIGS. 18-20.

What is claimed is:

1. A staining mixture comprising viable spermatozoa, a buffer solution, pyruvate, and a DNA selective dye, the concentration of the pyruvate being about 15 mM to about 50 mM.

2. The staining mixture of claim 1, wherein the mixture further comprises a composition selected from the group consisting of vitamin K, lipoic acid, glutathione, flavins, quinones, superoxide dismutase, superoxide dismutase mimics, and any combinations thereof.

3. The staining mixture of claim 2, wherein the mixture further comprises a composition selected from the group consisting of vitamin K, lipoic acid, and combinations thereof.

4. The staining mixture of claim 1, wherein the composition comprises pyruvate at a concentration selected from a group consisting of about 15 mM, about 25 mM, and about 50 mM.

5. The staining mixture of claim 2, wherein the composition comprises vitamin K at a concentration selected from the group consisting of about 10 µM, about 50 µM, about 75 µM, and about 100 µM.

6. The staining mixture of claim 2, wherein the composition comprises lipoic acid at a concentration selected from the group consisting of about 0.1 mM, about 0.5 mM, about 0.75 mM, about 1.0 mM, and about 1.5 mM.

7. The staining mixture of claim 1, wherein the DNA selective dye is a DNA selective fluorescent dye.

8. The staining mixture of claim 2, wherein the DNA selective dye is a DNA selective fluorescent dye.

9. The staining mixture of claim 1, wherein the dye is a UV excitable or a visible light excitable dye.

10. The staining mixture of claim 2, wherein the dye is a UV excitable or a visible light excitable dye.

11. The staining mixture claim 1, wherein the dye is selected from the group consisting of Hoechst 33342, Hoechst 33258, SYBR-14, and bisbenzimide-BOD1PY® conjugate 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl{3-[({4-[6-(4-methylpiperazin-1-yl)-1H,3'H-2,5'-bibenzimidazol-2'-yl]phenoxy}acetyl)amino]propyl}amino)propyl]hexanamide.

12. The staining mixture claim 2, wherein the dye is selected from the group consisting of Hoechst 33342, Hoechst 33258, SYBR-14, and bisbenzimide-BOD1PY® conjugate 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl{3-[({4-[6-(4-methylpiperazin-1-yl)-1H,3'H-2,5'-bibenzimidazol-2'-yl]phenoxy}acetyl)amino]propyl}amino)propyl]hexanamide.

13. The staining mixture of claim 1, wherein the staining mixture further comprises a buffer that inhibits sperm motility.

14. The staining mixture of claim 2, wherein the staining mixture further comprises a buffer that inhibits sperm motility.

15. The staining mixture of claim 13, wherein the buffer is a carbonate-based buffer.

16. The staining mixture of claim 14, wherein the buffer is a carbonate-based buffer.

17. The staining mixture of claim 13, wherein the buffer comprises 0.097 moles/L of $NaHCO_3$, 0.173 moles/L of $KHCO_3$, 0.090 moles/L $C_6H_8O_7 \cdot H_2O$ in water.

18. The staining mixture of claim 1, wherein the composition comprises pyruvate at a concentration of about 15 mM to about 40 mM.

19. The staining mixture of claim 1, wherein the composition comprises pyruvate at a concentration of above about 15 mM to about 20 mM.

20. The staining mixture of claim 1, wherein the composition comprises pyruvate at a concentration of 25 mM to about 50 mM.

21. The staining mixture of claim 1, wherein the buffer is selected from a group consisting of: a TRIS and citric acid monohydrate buffer, a TRIS and TES buffer, a Sodium Citrate buffer, and a HEPEs buffer.

22. A staining mixture comprising viable bovine spermatozoa, pyruvate, and a DNA selective dye, the concentration of the pyruvate being about 15 mM to about 50 mM.

* * * * *